(12) United States Patent
Mittleman et al.

(10) Patent No.: US 7,531,803 B2
(45) Date of Patent: May 12, 2009

(54) METHOD AND SYSTEM FOR TRANSMITTING TERAHERTZ PULSES

(75) Inventors: Daniel M. Mittleman, Houston, TX (US); Jason A. Deibel, Dayton, OH (US); Matthew Escarra, Princeton, NJ (US)

(73) Assignee: William Marsh Rice University, Houston, TX (US)

( * ) Notice: Subject to any disclaimer, the term of this patent is extended or adjusted under 35 U.S.C. 154(b) by 0 days.

(21) Appl. No.: 11/777,684

(22) Filed: Jul. 13, 2007

(65) Prior Publication Data

US 2008/0023633 A1      Jan. 31, 2008

Related U.S. Application Data

(60) Provisional application No. 60/807,380, filed on Jul. 14, 2006.

(51) Int. Cl.
  *G01N 21/35* (2006.01)
  *H01P 3/02* (2006.01)
(52) U.S. Cl. .................. 250/341.1; 333/239
(58) Field of Classification Search ............. 333/239; 250/341.1
   See application file for complete search history.

(56) References Cited

U.S. PATENT DOCUMENTS

| | | | |
|---|---|---|---|
| 4,303,900 A * | 12/1981 | Tourneur | 333/239 |
| 5,729,017 A | 3/1998 | Brener et al. | |
| 5,894,125 A * | 4/1999 | Brener et al. | 250/330 |
| 5,939,721 A | 8/1999 | Jacobsen et al. | |
| 5,952,818 A | 9/1999 | Zhang et al. | |
| 6,476,596 B1 | 11/2002 | Wraback et al. | |
| 6,665,075 B2 | 12/2003 | Mittleman et al. | |
| 6,690,001 B2 | 2/2004 | Jiang et al. | |
| 6,734,974 B2 | 5/2004 | Jiang et al. | |
| 6,815,683 B2 | 11/2004 | Federici et al. | |
| 2007/0164842 A1* | 7/2007 | Koenig | 333/219.2 |

FOREIGN PATENT DOCUMENTS

WO      WO 9641351 A1 * 12/1996
WO      WO 2006019776 A2 *  2/2006

OTHER PUBLICATIONS

Wang, K. and D. M. Mittleman, "Metal wires for terahertz wave guiding," Nature, Nov. 18, 2004, vol. 432, pp. 376-379.*

(Continued)

*Primary Examiner*—Constantine Hannaher
(74) *Attorney, Agent, or Firm*—Conley Rose, P.C.; Rodney B. Carroll

(57) ABSTRACT

Systems for THz transmission using new types of THz waveguides with low loss, negligible group velocity dispersion and structural simplicity are described herein. The THz system incorporates the use of a waveguide with two or more substantially parallel conductive elements which may enable many new THz sensing applications. It is now possible to direct the THz pulse inside of containers or around corners, where line-of-sight optics are not practical. Moreover, the systems allow use of either radially polarized or linearly polarized THz antennas. The disclosed systems are compatible with existing terahertz generation and detection techniques.

28 Claims, 13 Drawing Sheets

OTHER PUBLICATIONS

Ralph, Stephen E., et al., "Trap-enhanced electric fields in semi-insulators: the role of electrical and optical carrier injection," Appl. Phys. Lett., Oct. 14, 1991, pp. 1972-1974, vol. 59, No. 16, American Institute of Physics.

Research@Rice, "Keep your pants (and your shoes) on—T-rays may simplify airport screening," T-Ray [Terahertz] Wave Guide, http://explore.rice.edu/explore/research_archive.asp, 1 page, Dec. 2004.

Rochat, Michel, et al., "Low-threshold terahertz quantum-cascade lasers," Applied Physics Letters, Aug. 19, 2002, pp. 1381-1383, vol. 81, No. 8, American Institute of Physics.

Roux, Jean-François, et al., "Grating-assisted coupling of terahertz waves into a dielectric waveguide studied by terahertz time-domain spectroscopy," Applied Optics, Oct. 20, 2002, pp. 6507-6513, vol. 41, No. 30, Optical Society of America.

Rudd, J. V., et al., "Compact, fiber-pigtailed, terahertz imaging system," Proceedings of SPIE vol. 3934, 2000, pp. 27-35.

Rudd, J. Van, et al., "Cross-polarized angular emission patterns from lens-coupled terahertz antennas," J. Opt. Soc. Am. B, Oct. 2001, pp. 1524-1533, vol. 18, No. 10, Optical Society of America.

Rudd, J. Van, et al., "Influence of substrate-lens design in terahertz time-domain spectroscopy," J. Opt. Soc. Am. B, Feb. 2002, pp. 319-329, vol. 19, No. 2, Optical Society of America.

Rudd, J. V., et al., "Quadrupole radiation from terahertz dipole antennas," Optics Letters, Oct. 15, 2000, pp. 1556-1558, vol. 25, No. 20, Optical Society of America.

Samuels, Alan C., et al., "Environmental sensing of chemical and biological warfare agents in the THz region," International Journal of High Speed Electronics and Systems, 2002, pp. 273-283, vol. 12, No. 2, World Scientific Publishing Company.

Schmitt, Ron, "Understanding electromagnetic fields and antenna radiation takes (almost) no math," www.ednmag.com, Mar. 2, 2000, pp. 77, 78, 80, 82, 84, 86, and 88, EDN.

Senior, John M., "Optical fiber communications: principles and practice," 1985, 2 pages, Prentice-Hall International, Inc., London, title, copyright, and first contents pages only.

Shi, Wei, et al., "Designs of terahertz waveguides for efficient parametric terahertz generation," Applied Physics Letters, Jun. 23, 2003, pp. 4435-4437, vol. 82, No. 25, American Institute of Physics.

Siegel, Peter H., et al., "2.5-THz GaAs monolithic membrane-diode mixer," IEEE Transactions on Microwave Theory and Techniques, May 1999, pp. 596-604, vol. 47, No. 5, IEEE.

Smith, Peter R., et al., "Subpicosecond photoconducting dipole antennas," IEEE Journal of Quantum Electronics, Feb. 1988, pp. 255-260, vol. 24, No. 2, IEEE.

Suhara, Toshiaki, et al., "Theoretical analysis of laterally emitting terahertz-wave generation by difference-frequency generation in channel waveguides," IEEE Journal of Quantum Electronics, Jan. 2003, pp. 166-171, vol. 39, No. 1, IEEE.

Tani, M. et al., "Photoconductive terahertz transceiver," Electronics Letters, Apr. 27, 2000, pp. 804-805, vol. 36, No. 9, IEE.

Tani, M., et al., "Photoconductive twin dipole antennas for THz transceiver," Electronics Letters, Jan. 3, 2002, pp. 5-6, vol. 38, No. 1, IEE.

Tassaing, Thierry, et al., "A far infrared study of water diluted in hydrophobic solvents," Molecular Physics, 1995, pp. 769-785, vol. 84, No. 4, Taylor & Francis Ltd.

Tassaing, T., et al., "Vibrational spectroscopic studies of the chemical dynamics in charge transfer complexes of the type iodine—pyridine 2. Intermolecular dynamics from far infrared bands," Molecular Physics, 1997, pp. 281-292, vol. 92, No. 2, Taylor & Francis Ltd.

Tyrrell, James, "Terahertz wired up and ready to go," optics.org, http://optics.org/cws/article/research/20948, Nov. 26, 2004, 2 pages.

Van Der Valk, N. C. J., et al., "Electro-optic detection of subwavelength terahertz spot sizes in the near field of a metal tip," Applied Physics Letters, Aug. 26, 2002, pp. 1558-1560, vol. 81, No. 9, American Institute of Physics.

Van Exter, Martin, et al., "Characterization of an optoelectronic terahertz beam system," IEEE Transactions on Microwave Theory and Techniques, Nov. 1990, pp. 1684-1691, vol. 38, No. 11, IEEE.

Verghese, S., et al., "Generation and detection of coherent terahertz waves using two photomixers," Applied Physics Letters, Dec. 28, 1998, pp. 3824-3826, vol. 73, No. 26, American Institute of Physics.

Wang, Kanglin, et al., "Antenna effects in terahertz apertureless near-field optical microscopy," Applied Physics Letters, Oct. 4, 2004, pp. 2715-2717, vol. 85, No. 14, American Institute of Physics.

Wang, Kanglin, et al., "Guided propagation of terahertz pulses on metal wires," J. Opt. Soc. Am. B, Sep. 2005, pp. 2001-2008, vol. 22, No. 9, Optical Society of America.

Wang, Kanglin, et al., "Propagation effects in apertureless near-field optical antennas," Applied Physics Letters, Jan. 12, 2004, pp. 305-307, vol. 84, No. 2, American Institute of Physics.

Weling, Aniruddha S., et al., "Novel sources and detectors for coherent tunable narrow-band terahertz radiation in free space," J. Opt. Soc. Am. B, Dec. 1996, pp. 2783-2791, vol. 13, No. 12, Optical Society of America.

Williams, Benjamin S., et al., "Terahertz quantum-cascade laser at $\lambda \approx 100$ μm using metal waveguide for mode confinement," Applied Physics Letters, Sep. 15, 2003, pp. 2124-2126, vol. 83, No. 11, American Institute of Physics.

Woodward, Ruth M., et al., "Terahertz pulse imaging in reflection geometry of human skin cancer and skin tissue," Physics in Medicine and Biology, 2002, pp. 3853-3863, vol. 47, IOP Publishing Ltd, United Kingdom.

Woolard, D. L., et al., "Submillimeter-wave phonon modes in DNA macromolecules," pp. 051903-1 to 051903-11, vol. 65, Physical Review E, 2002.

Woolard, D., et al., "Terahertz electronics for chemical and biological warfare agent detection," 1999, pp. 925-928, IEEE MTT-S Digest.

Wu, Q., et al., "Dynamic range of an electro-optic field sensor and its imaging applications," Appl. Phys. Lett., Jun. 3, 1996, pp. 3224-3226, vol. 68, No. 23, American Institute of Physics.

Wu, Q., et al., "Free space electro-optics sampling of mid-infrared pulses," Appl. Phys. Lett., Sep. 8, 1997, pp. 1285-1286, vol. 71, No. 10, American Institute of Physics.

Wu, Q., et al., "Two-dimensional electro-optic imaging of THz beams," Appl. Phys. Lett., Aug. 19, 1996, pp. 1026-1028, vol. 69, No. 8, American Institute of Physics.

Xu, L., et al., "Terahertz beam generation by femtosecond optical pulses in electro-optic materials," Appl. Phys. Lett., Oct. 12, 1992, pp. 1784-1786, vol. 61, No. 15, American Institute of Physics.

Yasui, Takeshi, et al., "Asynchronous optical sampling terahertz time-domain spectroscopy for ultrahigh spectral resolution and rapid data acquisition," Applied Physics Letters, 2005, pp. 061101-1 to 061101-3, vol. 87, American Institute of Physics.

Zhao, G., et al., "Design and performance of a THz emission and detection setup based on a semi-insulating GaAs emitter," Review of Scientific Instruments, Apr. 2002, pp. 1715-1719, vol. 73, No. 4, American Institute of Physics.

Zhao, Guozhong, et al., "Terahertz dielectric properties of polystyrene foam," J. Opt. Soc. Am. B, Jun. 2002, pp. 1476-1479, vol. 19, No. 6, Optical Society of America.

Ajili, L., et al., "Continuous-wave operation of far-infrared quantum cascade lasers," Electronics Letters, Dec. 5, 2002, pp. 1675-1676, vol. 38, No. 25, IEE.

Aquistapace, F., et al., "Photovariation of grating-assisted coupling of terahertz waves into a silicon waveguide," Journal of Applied Physics, Dec. 15, 2003, pp. 7888-7891, vol. 94, No. 12, American Institute of Physics.

Alonso, Kevin, et al., "Use of Goubau line to couple microwave signals generated by resonant laser-assisted field emission," Ultramicroscopy, 1999, pp. 175-179, vol. 79, Elsevier Science B.V.

Armstrong, Darrell J., et al., "Generation of radially polarized beams with an image-rotating resonator," Applied Optics, Jun. 20, 2003, pp. 3550-3554, vol. 42, No. 18, Optical Society of America.

Auston, D.H., et al., "Picosecond photoconducting Hertzian dipoles," Appl. Phys. Lett., Aug. 1, 1984, pp. 284-286, vol. 45, No. 3, American Institute of Physics.

Becker, James P., et al., "A finite ground coplanar line-to-silicon micromachined waveguide transition," IEEE Transactions on Microwave Theory and Techniques, Oct. 2001, pp. 1671-1676, vol. 49, No. 10, IEEE.

Berger, Eric, "Researchers exploring T-rays' uses, benefits," Nov. 23, 2004, 1 page, Houston Chronicle.

Birch, J. R., et al., "The optical constants of some common low-loss polymers between 4 and 40 cm-1," Infrared Physics, 1981, pp. 225-228, vol. 21, Pergamon Press Ltd, Great Britain.

Bishop, Jennifer A., et al., "Monolithic coaxial transmission lines for mm-wave ICs," 1991, pp. 252-260, IEEE.

Bomzon, Ze'ev, et al., "Formation of radially and azimuthally polarized light using space-variant subwavelength metal stripe gratings," Applied Physics Letters, Sep. 10, 2001, pp. 1587-1589, vol. 79, No. 11, American Institute of Physics.

Boyd, Jade, "Rice engineers demo first T-ray endoscope," EurekAlert?, http://www.eurekalert.org/pub_releases/2004-11/ru-red111004.php, Nov. 17, 2004, 2 pages.

Boyd, Joel E., et al., "Terahertz vibrational modes of inverse micelles," J. Phys. Chem. B, 2002, pp. 6346-6353, vol. 106, No. 24, American Chemical Society.

Boyd, Joel E., et al., "Direct observation of terahertz surface modes in nanometer-sized liquid water pools," Physical Review Letters, Oct. 1, 2001, pp. 147401-1 to 147401-4, vol. 87, No. 14, The American Physical Society.

Bromage, Jake, et al., "Spatiotemporal shaping of half-cycle terahertz pulses by diffraction through conductive apertures of finite thickness," J. Opt. Soc. Am. B, Apr. 1998, pp. 1399-1405, vol. 15, No. 4, Optical Society of America.

Brown, Chappell, "Waveguide principle found for terahertz imaging," EETimes, http://www.eetimes.com/showArticle.jhtml?articleID=54200109&printable=true, Nov. 23, 2004, 2 pages, Copyright 2007 by CMP Media LLC.

Cai, Y., et al., "Design and performance of singular electric field terahertz photoconducting antennas," Appl. Phys. Lett., Oct. 13, 1997, pp. 2076-2078, vol. 71, No. 15, American Institute of Physics.

Chantry, George W., "Long-wave optics: The science and technology of infrared and near-millimetre waves; vol. 1: Principles," 1984, 2 pages, Academic Press Inc., Harcourt Brace Jovanovich, Inc., USA, Title, copyright, and dedication pages only.

Chen, Hou-Tong, et al., "Terahertz imaging with nanometer resolution," Applied Physics Letters, Oct. 13, 2003, pp. 3009-3011, vol. 83, No. 15, American Institute of Physics.

Choi, Charles, "Wave on a wire, " ScienceNOW, http://sciencenow.sciencemag.org/cgi/content/full/2004/1117/2, Nov. 17, 2004, 2 pages, American Association for the Advancement of Science.

Coleman, S., et al., "A THz transverse eletromagnetic mode two-dimensional interconnect layer incorporating quasi-optics," Applied Physics Letters, Nov. 3, 2003, pp. 3656-3658, vol. 83, No. 18, American Institute of Physics.

Collins, C. E., et al., "A new micro-machined millimeter-wave and terahertz snap-together rectangular waveguide technology," IEEE Microwave and Guided Wave Letters, Feb. 1999, pp. 63-65, vol. 9, No. 2, IEEE.

Davis, Nicole, "T-rays hard to handle? Not anymore," Feb. 2005, p. 40, Popular Science.

Deibel, Jason A., et al., "Enhanced coupling of terahertz radiation to cylindrical wire waveguides," Optics Express, Jan. 9, 2006, pp. 279-290, vol. 14, No. 1, OSA.

Deibel. J. A., et al., "Photoconductive terahertz antenna with radial symmetry," Electronics Letters, Mar. 3, 2005, 2 pages, vol. 41, No. 5, IEE.

Digby, John W., et al., "Fabrication and characterization of micromachined rectangular waveguide components for use at millimeter-wave and terahertz frequencies," IEEE Transactions on Microwave Theory and Techniques, Aug. 2000, pp. 1293-1302, vol. 48, No. 8, IEEE.

DOE-NSF-NIH workshop on opportunities in THz science, Feb. 12-14, 2004, pp. 1-123 plus 1 cover page, Arlington, Virginia.

Dorn, R., et al., "Sharper focus for a radially polarized light beam," Physical Review Letters, Dec. 5, 2003, pp. 233901-1 to 233901-4, vol. 91. No. 23, The American Physical Society.

Dorney, Timothy D., et al., "Material parameter estimation with terahertz time-domain spectroscopy," J. Opt. Soc. Am. A, Jul. 2001, pp. 1562-1571, vol. 18, No. 7, Optical Society of America.

Dorney, Timothy D., et al., "Single-cycle terahertz electromagnetic pulses: A new test bed for physical seismic modeling," Geophysics, Jan.-Feb. 2003, pp. 308-313, vol. 68, No. 1, Society of Exploration Geophysicists.

Dorney, Timothy D., et al., "Terahertz reflection imaging using Kirchhoff migration," Optics Letters, Oct. 1, 2001, pp. 1513-1515, vol. 26, No. 19, Optical Society of America.

Dorney, Timothy D., et al., Terahertz multistatic reflection imaging, J. Opt. Soc. Am. A, Jul. 2002, pp. 1432-1442, vol. 19, No. 7, Optical Society of America.

Dykaar, Douglas R., et al., "High-frequency characterization of thin-film Y-Ba-Cu oxide superconducting transmission lines," Appl. Phys. Lett., Apr. 25, 1988, pp. 1444-1446, vol. 52, No. 17, American Institute of Physics.

Fattinger, Ch., et al., "Terahertz beams," Appl. Phys. Lett., Feb. 6, 1989, pp. 490-492, vol. 54, No. 6, American Institute of Physics.

Fischer, Anne L., "Waveguide has been developed for terahertz waves," Photonics.com, http://www.photonics.com//content/spectra/2005/January/tech/79929.aspx, Jan. 1, 2005, 2 pages.

Flinn, Gregory, "Terahertz radiation finds a place in biomedicine," May 2005, pp. 40-43 plus 1 cover page, Biophotonics International, A Laurin Publication.

Focardi, Paolo, et al., "Coplanar-waveguide-based terahertz hot-electron-bolometer mixers—improved embedding circuit description," IEEE Transactions on Microwave Theory and Techniques, Oct. 2002, pp. 2374-2383, vol. 50, No. 10, IEEE.

Frankel, Michael Y., et al., "Terahertz attenuation and dispersion characteristics of coplanar transmission lines," IEEE Transactions on Microwave Theory and Techniques, Jun. 1991, pp. 910-916, vol. 39, No. 6, IEEE.

Gallagher, W. J., et al., "Subpicosecond optoelectronic study of resistive and superconductive transmission lines," Appl. Phys. Lett., Feb. 9, 1987, pp. 350-352, vol. 50, No. 6, American Institute of Physics.

Gallot, G., et al., "Terahertz waveguides," J. Opt. Soc. Am. B, May 2000, pp. 851-863, vol. 17, No. 5, Optical Society of America.

Greene, B. I., et al., "Far-infrared light generation at semiconductor surfaces and its spectroscopic applications," IEEE Journal of Quantum Electronics, Oct. 1992, pp. 2302-2312, vol. 28, No. 10, IEEE.

Grischkowsky, D., et al., "Electromagnetic shock waves from transmission lines," Physical Review Letters, Oct. 12, 1987, pp. 1663-1666, vol. 59, No. 15, The American Physical Society.

Grischkowsky, Daniel R., "Optoelectronic characterization of transmission lines and waveguides by terahertz time-domain spectroscopy," IEEE Journal on Selected Topics in Quantum Electronics, Nov./Dec. 2000, pp. 1122-1135, vol. 6, No. 6, IEEE.

Grosjean, T., et al., "An all-fiber device for generating radially and other polarized light beams," Optics Communications, Mar. 1, 2002, pp. 1-5, Elsevier Science B.V.

Hadjiloucas, Sillas, et al., "Measurement of propagation constant in waveguides with wideband coherent terahertz spectroscopy," J. Opt. Soc. Am. B, Feb. 2003, pp. 391-401, vol. 20, No. 2, Optical Society of America.

Han, H., et al., "Terahertz pulse propagation in plastic photonic crystal fibers," 2002, pp. 1075-1078, IEEE, MTT-S Digest.

Han, H., et al., "Terahertz pulse propagation in plastic photonic crystal fiber," Applied Physics Letters, Apr. 15, 2002, pp. 2634-2636, vol. 80, No. 15, American Institute of Physics.

Heiliger, H.-M., et al., "Low-dispersion thin-film microstrip lines with cyclotene (benzocyclobutene) as dielectric medium," Appl. Phys. Lett., Apr. 28, 1997, pp. 2233-2235, vol. 70, No. 17, American Institute of Physics.

Hu, B. B., et al., "Imaging with terahertz waves," Optics Letters, Aug. 15, 1995, pp. 1716-1718 plus 2 images, vol. 20, No. 16, Optical Society of America.

Hu, B. B., et al., "Terahertz radiation induced by subband-gap femtosecond optical excitation of GaAs," Nov. 4, 1991, pp. 2709-2712, vol. 67, No. 19, The American Physical Society.

Huynh, NGOC-HOA, et al., "FDTD analysis of submillimeter-wave CPW with finite-width ground metallization," IEEE Microwave and Guided Wave Letters, Dec. 1997, pp. 414-416, vol. 7, No. 12, IEEE.

Inan, Umran S., et al., "Electromagnetic waves," 2000, 2 pages, Prentice Hall, USA, Title, copyright, and dedication pages only.

Inouye, Yasushi, et al., "Near-field scanning optical microscope with a metallic probe tip," Optics Letters, Feb. 1, 1994, pp. 159-161, vol. 19, No. 3, Optical Society of America.

Jackson, R. H., et al., "Design of a far-infrared CHI wiggler free-electron laser," Nuclear Instruments and Methods in Physics Research A, 1996, pp. 226-229, vol. 375, Elsevier Science B.V.

Jacobsen, R. H., et al., "Chemical recognition of gases and gas mixtures with terahertz waves," Optics Letters, Dec. 15, 1996, pp. 2011-2013, vol. 21, No. 24, Optical Society of America.

Jamison, S. P., et al., "Single-mode waveguide propagation and reshaping of sub-ps terahertz pulses in sapphire fibers," Applied Physics Letters, Apr. 10, 2000, pp. 1987-1989, vol. 76, No. 15, American Institute of Physics.

Jepsen, P. Uhd, et al., "Generation and detection of terahertz pulses from biased semiconductor antennas," J. Opt. Soc. Am. B, Nov. 1996, pp. 2424-2436, vol. 13, No. 11, Optical Society of America.

Jian, Zhongping, et al., "Characterizing individual scattering events by measuring the amplitude and phase of the electric field diffusing through a random medium," Physical Review Letters, Jul. 18, 2003, pp. 033903-1 to 033903-4, vol. 91, No. 3, The American Physical Society.

Johnson, Jon L., et al., "Enhanced depth resolution in terahertz imaging using phase-shift interferometry," Applied Physics Letters, Feb. 5, 2001, pp. 835-837, vol. 78, No. 6, American Institute of Physics.

Johnson, Jon L., et al., "Interferometric imaging with terahertz pulses," IEEE Journal on Selected Topics in Quantum Electronics, Jul./Aug. 2001, pp. 592-599, vol. 7, No. 4, IEEE.

Kao, K. C., "The theory and practice of quasi-optical waveguide components," Proceedings of the Symposium on Quasi-Optics, Jun. 8-10, 1964, pp. 497-515 plus 1 cover page, Interscience Publisher, A Division of John Wiley & Sons, Inc.

Kawase, Kodo, et al., "Arrayed silicon prism coupler for a terahertz-wave parametric oscillator," Applied Optics, Mar. 20, 2001, pp. 1423-1426, vol. 40, No. 9, Optical Society of America.

Keiding, S. R., "Dipole correlation functions in liquid benzenes measured with terahertz time domain spectroscopy," J. Phys. Chem. A, 1997, pp. 5250-5254, vol. 101, No. 29, American Chemical Society.

Keilmann, F., et al., "Extreme sub-wavelength resolution with a scanning radio-frequency transmission microscope," Optics Communications, Aug. 1, 1996, pp. 15-18, vol. 129, Elsevier Science B.V.

Kindt, J. T., et al., "Far-infrared dielectric properties of polar liquids probed by femtosecond terahertz pulse spectroscopy," J. Phys. Chem., 1996, pp. 10373-10379, vol. 100, No. 24, American Chemical Society.

Knoll, B., et al., "Near-field probing of vibrational absorption for chemical microscopy," Nature, May 13, 1999, pp. 134-137, vol. 399, Macmillan Magazines Ltd.

Köhler, Rüdeger, et al., "Terahertz semiconductor-heterostructure laser," Nature, May 9, 2002, pp. 156-159, vol. 417, Macmillan Magazines Ltd.

Konorov, S. O., et al., "Waveguide modes of electromagnetic radiation in hollow-core microstructure and photonic-crystal fibers," Journal of Experimental and Theoretical Physics, 2003, pp. 857-869, vol. 96, No. 5, MAIK "Nauka/Interperiodica."

Kurtz, David S., et al., "Submillimeter-wave sideband generation using varactor Schottky diodes," IEEE Transactions on Microwave Theory and Techniques, Nov. 2002, pp. 2610-2617, vol. 50, No. 11, IEEE.

Lloyd, James, et al., "Characterization of apparent superluminal effects in the focus of an axicon lens using terahertz time-domain spectroscopy," 2003, pp. 289-294, vol. 219, Elsevier Science B.V.

Lubecke, Victor M., et al., Micromachining for terahertz applications, IEEE Transactions on Microwave Theory and Techniques, Nov. 1998, pp. 1821-1831, vol. 46, No. 11, IEEE.

Lukosz, W., et al., "Light emission by magnetic and electric dipoles close to a plane dielectric interface. II. Radiation patterns of perpendicular oriented dipoles," J. Opt. Soc. Am., Dec. 1977, pp. 1615-1619, vol. 67, No. 12, Optical Society of America.

Marcuvitz, N., "Waveguide handbook," 1951, 2 pages, McGraw-Hill Book Company, Inc., USA. Title, copyright, and first preface pages only.

McGowan, R. W., et al., "Propagation of ultrawideband short pulses of terahertz radiation through submillimeter-diameter circular waveguides," Optics Letters, Oct. 15, 1999, pp. 1431-1433, vol. 24, No. 20, Optical Society of America.

Mendis, R., et al., "Plastic ribbon THz waveguides," Journal of Applied Physics, Oct. 1, 2000, pp. 4449-4451, vol. 88, No. 7, American Institute of Physics.

Mendis, R., et al., "THz interconnect with low-loss and low-group velocity dispersion," IEEE Microwave and Wireless Components Letters, Nov. 2001, pp. 444-446, vol. 11, No. 11, IEEE.

Mendis, R., et al., "Undistorted guided-wave propagation of subpicosecond terahertz pulses," Optics Letters, Jun. 1, 2001, pp. 846-848, vol. 26, No. 11, Optical Society of America.

Mittleman, D. M. et al., "Noncontact semiconductor wafer characterization with the terahertz Hall effect," Appl. Phys. Lett., Jul. 7, 1997, pp. 16-18, vol. 71, No. 1, American Institute of Physics.

Mittleman, D. M., et al., "Recent advances in terahertz imaging," Appl Phys. B, 1999, pp. 1085-1094, vol. 68, Springer-Verlag.

Mittleman, Daniel, "Sensing with terahertz radiation," 2003, 2 pages, Springer-Verlag Berlin Heidelberg, Germany, Title, copyright, and first preface pages only.

Mittleman, Daniel M., et al., "T-ray imaging," IEEE Journal of Selected Topics in Quantum Electronics, Sep. 1996, pp. 679-692, vol. 2, No. 3, IEEE.

Mittleman, Daniel M., et al., "T-ray tomography," Optics Letters, Jun. 15, 1997, pp. 904-906, vol. 22, No. 12, Optical Society of America.

Miyaji, Godai, et al., "Intense longitudinal electric fields generated from transverse electromagnetic waves," Applied Physics Letters, May 10, 2004, pp. 3855-3857, vol. 84, No. 19, American Institute of Physics.

Moon, S. W., et al., "Terahertz waveguide components fabricated using a 3D x-ray microfabrication technique," Sep. 12, 1996, pp. 1794-1795, vol. 32, No. 19, Electronics Letters.

Moshe, Inon, et al., "Production of radially or azimuthally polarized beams in solid-state lasers and the elimination of thermally induced birefringence effects," Optics Letters, May 15, 2003, pp. 807-809, vol. 28, No. 10, Optical Society of America.

Mueller, Eric R., "Terahertz radiation: applications and sources," The Industrial Physicist, Aug./Sep. 2003, pp. 27-29, American Institute of Physics.

Nagel, M., et al., "Characterization of polypropylene thin-film microstrip lines at millimeter and submillimeter wavelengths," Microwave and Optical Technology Letters, Apr. 20, 2001, pp. 97-100, vol. 29, No. 2, John Wiley & Sons, Inc.

Nagel, Michael, et al., "Integrated planar terahertz resonators for femtomolar sensitivity label-free detection of DNA hybridization," Applied Optics, Apr. 1, 2002, pp. 2074-2078, vol. 41, No. 10, Optical Society of America.

National Research Council, Committee on Science and Technology for Countering Terrorism, Executive Summary, "Making the nation safer: The role of science and technology in countering terrorism," National Academies Press, 2002, pp. 273-303, National Academy of Sciences.

Nuss, Martin C., "Chemistry is right for T-ray imaging," Mar. 1996, pp. 25-30, IEEE.

Nuss, M. C., et al., "Terahertz electromagnetic radiation from quantum wells," Appl. Phys. B, 1994, pp. 249-259, vol. 58, Springer-Verlag.

Oron, Ram, et al., "The formation of laser beams with pure azimuthal or radial polarization," Applied Physics Letters, Nov. 20, 2000, pp. 3322-3324, vol. 77, No. 21, American Institute of Physics.

Patent application entitled "Method for coupling terahertz pulses into a coaxial waveguide" by Daniel Mittleman, et al., filed Jan. 28, 2008 as U.S. Appl. No. 11/572,090.

Pearce, Jeremy, et al., "Defining the Fresnel zone for broadband radiation," Physical Review E, 2002, pp. 056602-1 to 056602-4, vol. 66, The American Physical Society.

Pearce, Jeremy, et al., "Propagation of single-cycle terahertz pulses in random media," Optics Letters, Dec. 15, 2001, pp. 2002-2004, vol. 26, No. 24, Optical Society of America.

Pearce, Jeremy, et al., "Propagation of terahertz pulses in random media," Phil. Trans. R. Soc. Lond. A, 2004, pp. 301-314. vol. 362, The Royal Society.

Pearce, Jeremy, et al., "Scale model experimentation: using terahertz pulses to study light scattering," Physics in Medicine and Biology, 2002, pp. 3823-3830, vol. 47, IOP Publishing Ltd, United Kingdom.

Pearce, Jeremy, et al., "Statistics of multiply scattered broadband terahertz pulses," Physical Review Letters, Jul. 25, 2003, pp. 043903-1 to 043903-4, vol. 91, No. 4, The American Physical Society.

Pearce, Jeremy, et al., "Using terahertz pulses to study light scattering," Physica B, 2003, pp. 92-96, vol. 338, Elsevier B.V.

Peplow, Mark, "Simple wire picks up terahertz waves," news@nature.com, http://www.nature.com/news/2004/041115/full/04115-11.html, Nov. 17, 2004, 1 page.

Quabis, S., et al., "Focusing light to a tighter spot," Optics Communications, May 25, 2000, pp. 1-7, vol. 179, Elsevier Science B.V.

* cited by examiner

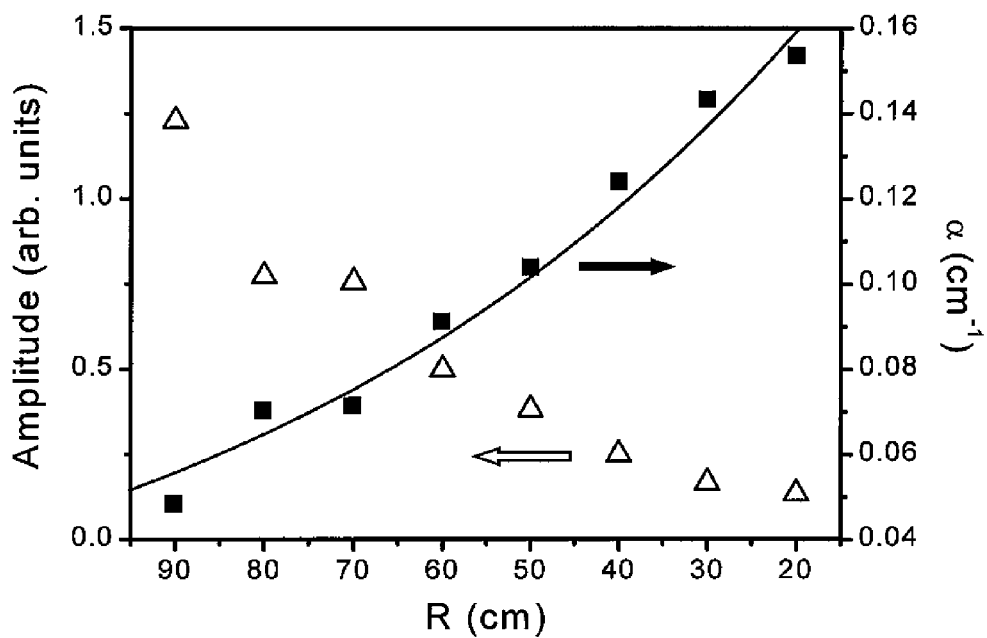
Fig. 18
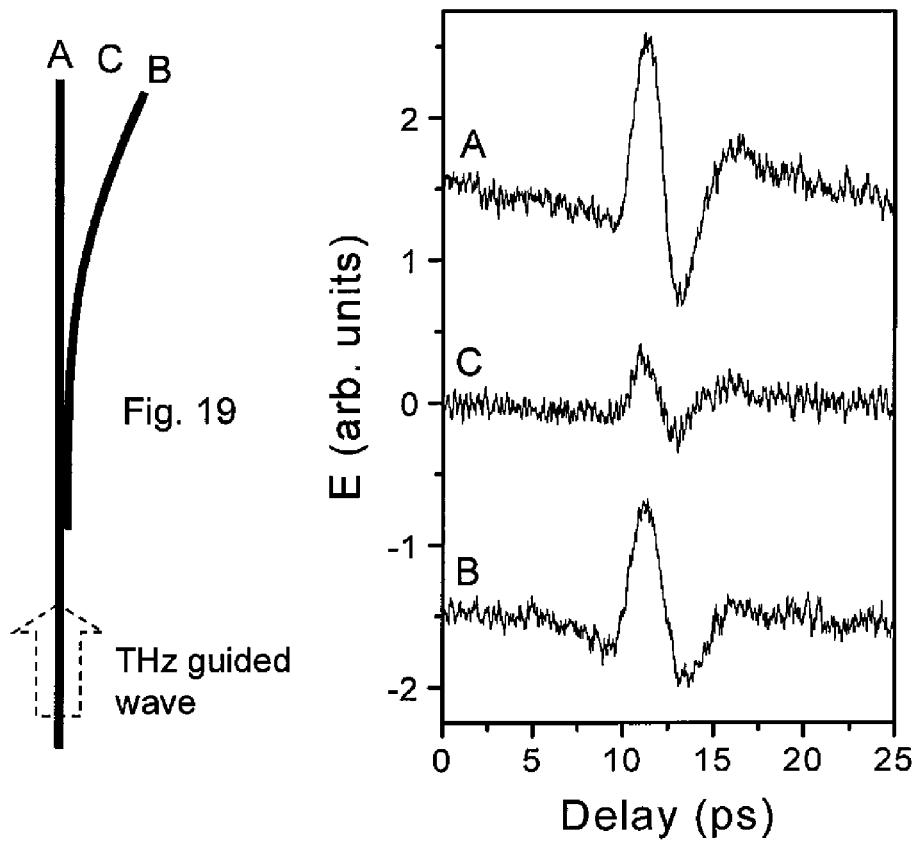
Fig. 19
Fig. 20

METHOD AND SYSTEM FOR TRANSMITTING TERAHERTZ PULSES

CROSS-REFERENCE TO RELATED APPLICATIONS

The present application claims the benefit of U.S. Provisional Application Ser. No. 60/807,380 filed Jul. 14, 2006, herein incorporated by reference in its entirety for all purposes.

TECHNICAL FIELD OF THE INVENTION

This invention provides a method and system for guiding terahertz pulses over practical distances with low loss and low dispersion.

BACKGROUND OF THE INVENTION

Rapid advances in laser technology have enabled various techniques for the generation and detection of electromagnetic radiation in the terahertz region (spanning from ~100 GHz to ~10 THz, or wavelengths between ~30 µm and ~3 mm). As a result, numerous uses of terahertz radiation have been explored, including trace gas detection, medical diagnosis, security screening, and defect analysis in complex materials such as space shuttle tiles. Many of these studies have relied on terahertz time-domain spectroscopy, a technique for generating sub-picosecond pulses with spectral content spanning much of the THz band.

However, progress is limited by the overwhelming reliance on free-space transport of the terahertz beam, using bulk optical components. In many real-world situations, the sample or region to be studied may not be readily accessible to a line-of-sight beam. Hence, common devices that operate at other wavelengths, such as optical fiber-based sensors or medical endoscopes rely on the guided wave delivery of light to the remote sensing location. In addition, while THz waves can be transmitted simply by free space propagation, free space propagation requires bulk optical components, which are difficult to align.

Thus, in order to expand the usefulness of THz radiation, it is desirable to provide optimized guided wave devices that operate at THz frequencies. The development of practical THz waveguides would dramatically expand the application of THz-TDS in areas such as gas sensing and nanometer thin-film measurements.

Heretofore, the development of THz waveguides has been hindered by the material properties and the application requirements in this spectral range. On the one hand, the characteristics of materials at THz frequencies make it extremely difficult to build a fiber to guide THz beams over a long distance. The most transparent materials for this range are crystalline (e.g., high resistivity silicon), and thus are costly, fragile, and challenging to form into specific geometries for waveguide configurations. Other materials, such as low-loss polymers or glasses, are more malleable but exhibit prohibitively high absorption losses for propagation distances of more than a few centimeters. For this reason, THz waveguides generally must rely on propagation in air, rather than via dielectric confinement as in an optical fiber.

On the other hand, many THz applications rely on the use of broadband pulses for time-domain analysis and spectroscopic applications. To avoid pulse reshaping during propagation, low dispersion is required. But for many conventional metal waveguides (e.g., metal tubes), pulse reshaping in propagation is difficult to avoid, due to the extreme dispersion near the waveguide cutoff frequencies. Furthermore, finite conductivity of metals can lead to considerable losses in the wave propagation.

Great efforts have been devoted to finding useful THz waveguides within the last few years, and various guides with quasi-optical coupling have been demonstrated. Most of these THz waveguides have been based on conventional guiding structures, such as metal tubes, plastic ribbons, or dielectric fibers. There have also been reports on the application of the latest technology of photonic crystal fibers to THz radiation. In all of these cases, the utility for transport of THz pulses is limited by group velocity dispersion of the guided waves.

The most promising studies have reported dispersionless propagation in parallel metal plate waveguides. Another type of dispersionless waveguide design is a ribbon waveguide, which is dispersionless and low-loss. In the parallel plate design, the loss is attributable to two factors: (1) lateral spreading due to the fact that the mode is unconfined in one of the two transverse dimensions, and (2) the finite conductivity of the metal used to confine the mode, which in this case results in a reported attenuation of ~80 dB/m. Furthermore, the attenuation is still unacceptably high, due in large part to the finite conductivity of the metal plates. In addition, the cross-sectional area of the waveguide is too large for many of the proposed THz applications, including in particular medical diagnostics. Consequently, there is a need for a waveguide that is effective at transmitting radiation at THz frequencies utilizing both linearly and radially polarized THz sources with low loss and dispersion while maintaining a low cross-sectional area for diagnostic and medical applications.

SUMMARY OF THE INVENTION

Systems for THz transmission using new types of THz waveguides with low loss, negligible group velocity dispersion and structural simplicity are described herein. The waveguides enable many new THz sensing applications. It is now possible to direct the THz pulse inside of containers or around corners, where line-of-sight optics are not practical. Moreover, the systems allow use of either radially polarized or linearly polarized THz antennas. The disclosed systems are compatible with existing terahertz generation and detection techniques. In some embodiments, a THz system includes the use of a coaxial antenna and a coaxial or uniaxial waveguide. In preferred embodiments, the THz system incorporates the use of a waveguide with two or more substantially parallel conductive elements. Further advantages and features of the systems and methods are described in more detail below.

In an embodiment, a terahertz (THz) transmitting system comprises an antenna capable of generating a beam of THz radiation. The system also comprises a waveguide aligned with the beam. The waveguide has at least a first and a second conductive elongate element in which the first and second conductive elongate elements are substantially parallel.

In another embodiment, a method for transmitting a terahertz signal comprises aligning an antenna capable of generating a beam of THz radiation with a waveguide comprising at least a first and second conductive element. The method further comprises generating a beam of THz radiation by focusing a laser at said antenna. In addition, the method comprises collimating and focusing said beam between the first and second conductive element of said waveguide. The method also comprises transmitting said beam along the length of said waveguide by propagating said beam between the first and second conductive element.

In yet another embodiment, a terahertz interferometer comprises a THz emitter that generates THz radiation. The interferometer also comprises a primary waveguide aligned with said emitter. The primary waveguide comprises at least a first and second conductive element where the at least first and second conductive element diverge to form a sample waveguide and a reference waveguide. Additionally, the interferometer comprises sample chamber where the sample waveguide passes through said sample chamber. The sample waveguide and said reference waveguide rejoin to form a secondary waveguide. Moreover, the interferometer comprises a detector capable of receiving THz radiation. The detector is aligned with the secondary waveguide.

Embodiments of a THz transmitting system further includes a metal waveguide with very simple geometry that may be used to guide broadband THz pulses with outstanding performance, including low loss and negligible group velocity dispersion. The guided propagation of THz pulses on a metal wire behaves similarly to the transverse electromagnetic (TEM) mode of a conventional coaxial waveguide. Since the exposed surface area of a wire is much smaller than that of any previously reported metal waveguide, the attenuation due to conductivity losses is extremely low for this configuration. The efficacy and structural simplicity of the disclosed waveguide present great advantages in the manipulation of guided THz radiation.

The foregoing has outlined rather broadly the features and technical advantages of embodiments of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of exemplary embodiments of the invention, reference will now be made to the accompanying drawings, in which:

FIG. 18 is a plot illustrating THz wave propagation on a 21 cm long wire waveguide with different bend radii R;

FIG. 19 is a schematic diagram of a simple Y-splitter structure, comprising a straight waveguide and a curved waveguide in contact with each other; and FIG. 20 is a plot of the THz waveforms detected at points A, B and C in FIG. 19;

DETAILED DESCRIPTION OF THE PREFERRED EMBODIMENTS

Certain terms are used throughout the following description and claims to refer to particular system components. In the following discussion and in the claims, the terms "including" and "comprising" are used in an open-ended fashion, and thus should be interpreted to mean "including, but not limited to . . . ."

As used herein, a waveguide is intended to refer to a device designed to confine and direct the propagation of electromagnetic waves.

Antenna

In order to efficiently couple radiation into a waveguide, it is desirable to match the spatial pattern (the mode) of the incident radiation to the mode of the waveguide. For a coaxial waveguide, this requires that the incident beam be radially polarized, since this is the characteristic of the waveguide mode with the lowest loss. Such a polarization profile is typically very difficult to generate for free-space radiation, which is why coaxial waveguides have not often been used at high frequencies. Embodiments of the THz system use components similar to those used in time-domain spectroscopy (TDS) to generate a radial mode profile through the use of a novel, radially symmetric antenna.

Figure 1:
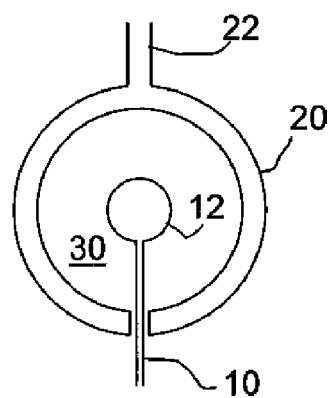
FIG. 1 is a schematic diagram of a coaxial antenna constructed in accordance with a first embodiment of the invention.

A first antenna configuration is illustrated in FIG. 1. A first, relatively narrow lead 10 extends in a first direction and terminates in a small circular electrode 12. A second lead 20 extends in an opposite direction and terminates in an annular electrode 22 that is concentric with circular electrode 12. While electrodes 12, 22 are shown as circular, they could alternatively be elliptical, oblong, polygonal, or any other non-circular shape. Likewise, lead 10 could extend farther, or even across the diameter of annular electrode 22, so as to provide another axis of symmetry in the antenna.

Figure 2:
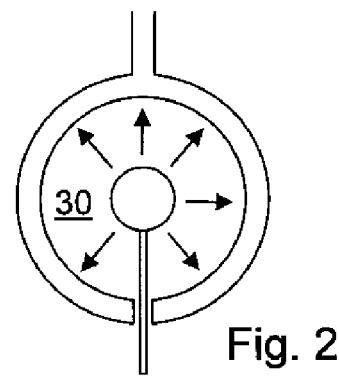
FIG. 2 is a schematic diagram of the coaxial antenna of FIG. 1 showing the mode of generation of radiation.

Electrodes 12, 22 are preferably formed on or adjacent to a semiconducting substrate so as to create a switch. A dc bias is placed across the antenna by applying a voltage across leads 10, 20 and an ultrashort pump-laser pulse (<100 femtosecond (fs)) is focused on the annular region 30 between electrodes 12, 22. The bias-laser pulse combination allows electrons to rapidly jump the gap, so when this region is excited by the application of a fs laser pulse the resulting current in the semiconductor produces a terahertz electromagnetic wave. This antenna operates in the same manner as a typical THz emitter antenna (commonly used in THz-TDS), except that the generated mode preserves the cylindrical symmetry of the antenna pattern and is therefore radially polarized, as illustrated by the arrows in FIG. 2. This radial mode is predicted to couple extremely efficiently (up to at least ~56%) into an optimized coaxial waveguide. Coaxial waveguides are discussed in detail below.

In this context, optimization of the waveguide entails selecting the dimensions of the coaxial waveguide (i.e., the inner and outer radii) to match the size of the radially polarized mode. This selection is preferably based on calculations of the mode matching for a given THz beam spot size.

It is possible to use a similar antenna design for photoconductive detection of the THz pulses emerging from a waveguide. This has the unique advantage that only the fundamental transverse electromagnetic (TEM) mode of the guide are detectable, so even if the launched wave were propagating in a multi-mode regime, this would not lead to measurable group velocity dispersion but only to increased propagation losses. Such considerations are important for any spectroscopic or imaging applications in which coaxial guides would be employed.

Coaxial Waveguide

Figure 3:
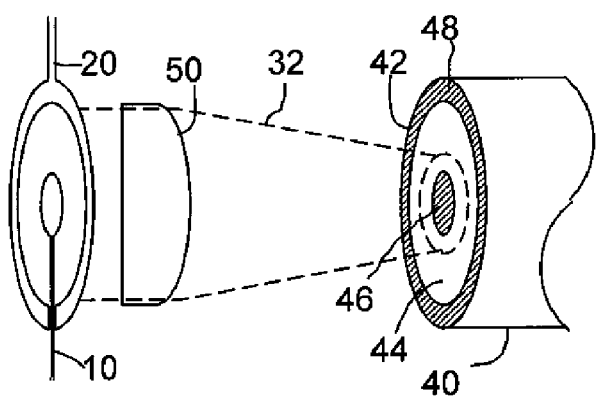
FIG. 3 is a schematic diagram of a coaxial antenna coupled to a coaxial waveguide.

As shown in FIG. 3, a coaxial waveguide 40 is preferably constructed with an inner core 46 and an outer wall 48 constructed from a material that is substantially opaque to terahertz radiation such as copper or any other highly conductive material. In embodiments, core 46 may be a wire and may be made of any suitable conductive material. Generally, core 46 is solid. However, it is contemplated that core 46 may be hollow or tubular. The annular region 44 between inner core 46 and outer wall 48 is preferably either evacuated or filled with a substance that is transparent or substantially transparent to terahertz radiation, such as a gas. Further details relating to a preferred construction for the waveguide are set out in detail below.

Still referring to FIG. 3, the radially polarized beam 32 generated by an antenna, such as that described above, can be coupled to a coaxial waveguide in any suitable manner. In one embodiment, beam 32 may be collimated and focused on one end 42 of coaxial waveguide 40. Beam 32 is preferably focused by a lens 50 such that a significant portion of its energy is incident on annular transmitting region 44. It is preferred that beam 32 not be focused too tightly, as that will result in too much of the energy being incident on core 46. Hence, it is preferred that the degree of focus be optimized. This optimization can be performed experimentally or mathematically.

In alternative embodiments, one or both of the electrodes of the antenna may be constructed on, attached directly to, or integral with the end of the waveguide. In these embodiments, circular electrode 12 may be attached to or formed by the end of the core of the waveguide and/or annular electrode 22 may be attached to or formed by the end of the outer wall of the waveguide. These embodiments avoid the need for collimation and/or focusing while providing coupling at a very high efficiency.

Figure 4:
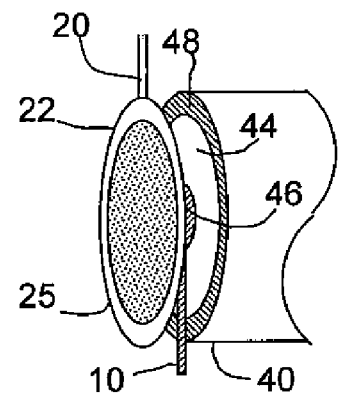
FIG. 4 is a schematic diagram of an alternative embodiment of an antenna coupled to a coaxial waveguide.

In an exemplary embodiment, shown in FIG. 4, an annular electrode 20 is spanned by a web of semiconducting material 25 and a lead 10 is provided to the end of core 46, which serves as the inner electrode. The fs laser pulse is applied to semiconductor 25 while a voltage is applied across the two electrodes. In other variations (not shown), the inner electrode rather than the outer electrode may be separate from the waveguide and may support a radially extending semiconducting web. Regardless of whether one, neither, or both of the electrodes is separate from the waveguide, a sheet or web of semiconducting material extends normal to the longitudinal axis of the waveguide and spans its cross-sectional area. Also, regardless of the configuration of the electrodes and waveguide, it is not necessary that the dimensions of electrode 12 coincide with those of the core of the waveguide or that the dimensions of annular electrode 22 coincide with those of the outer wall of the waveguide.

The emission properties of the antenna (the mode pattern and the fraction of the radiation coupled into the high-dielectric substrate) are preferably optimized with respect to the geometrical factors (inner and outer radii, line thicknesses, etc). This optimization can be performed numerically, using commercially available finite element analysis software or any other suitable algorithms.

Fabrication techniques suitable for making the antennas or antenna/waveguide combinations are similar to the techniques used to make conventional THz dipole antennas. Once fabricated, each antenna is coupled to an femtosecond optical excitation beam, preferably using fiber delivery (as has been done with some dipole antennas). An additional step may involve coupling or attaching these antennas directly to the input and output faces of the waveguide as described above, in order to achieve the highest possible levels of energy coupling into the guided mode.

Some embodiments of the waveguide include a core and outer wall, as described above. In addition, because some embodiments include an evacuated or gas-filled annulus, it is preferred in those embodiments to provide means for maintaining the core at the center of the waveguide. It is preferred that the inner conductor be positioned as precisely as possible along the axis of the outer cylinder so as to maximize symmetry of the waveguide and efficiency of transmission. This can be accomplished in any of several ways.

Figure 5:
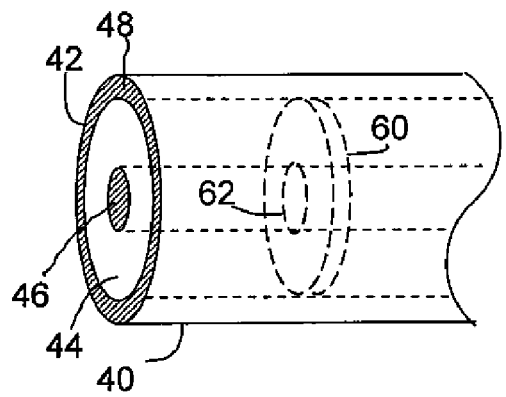
FIG. 5 is a schematic diagram of an alternative embodiment of a coaxial waveguide.

One approach, shown in phantom in FIG. 5, is to use a plurality of cylindrical plugs 60, spaced apart along the length of the waveguide cylinder, with holes 62 drilled in their centers through which the inner conductor is inserted. If these holes are positioned accurately and plugs 60 are sized correctly, plugs 60 will hold inner conductor 46 in precise coaxial alignment with outer wall 48. Plugs 60 are preferably composed of a material that has a low refractive index and is as nearly invisible to THz radiation as possible, such as rigid polystyrene foam, other polymeric foams, or, less preferably, non-foamed materials. Other means for supporting core 46 may be used, including but not limited to braces, fins, and legs.

In preferred embodiments, the waveguide is substantially straight. In alternative embodiments, the axis of the wave guide may include one or more curves, however it is expected that a curvilinear waveguide will result in some loss of efficiency, as some of the transmitted energy is lost to modes that are not compatible with the waveguide. More specifically, curves in the waveguide tend to convert from the TEM mode to other modes. These other modes are not detected by the radial receiver antenna, with the result that the detected energy is lower. Thus, bends introduce loss. It may be possible for the bend to also introduce dispersion, which is typically undesirable. Dispersion would involve coupling from the TEM mode into other modes, and then back again.

Uniaxial Waveguide

In still another embodiment, a waveguide for THz radiation may comprise only a conductive core 46. Because a significant portion of the losses in a coaxial waveguide are the result of the finite conductivity of the outer wall, while only a portion of the losses are due to dispersion (diffractive spreading), a waveguide comprising only a core 46 may transmit THz radiation sufficiently for some purposes, particularly over short distances (less than a few meters). It is further expected that such a uniaxial waveguide may include some degree of curvilinearity. Uniaxial waveguides in accordance with the invention may be constructed of any suitably conductive material, including but not limited to bare metal wire. In some embodiments, a bare metal wire with a thin dielectric coating may be advantageous in confining the mode closer to the surface of the wire. The material and diameter of the core may be optimized according to the desired operating parameters such as wavelength and transmission distance but is preferably between 0.1 and 30 mm in diameter, more preferably between 0.1 and 20 mm, and still more preferably 0.5 and 10 mm in diameter The uniaxial waveguides may also be used in plural, in a THz sensor such as that shown in FIG. 8 and described below.

Figure 12:
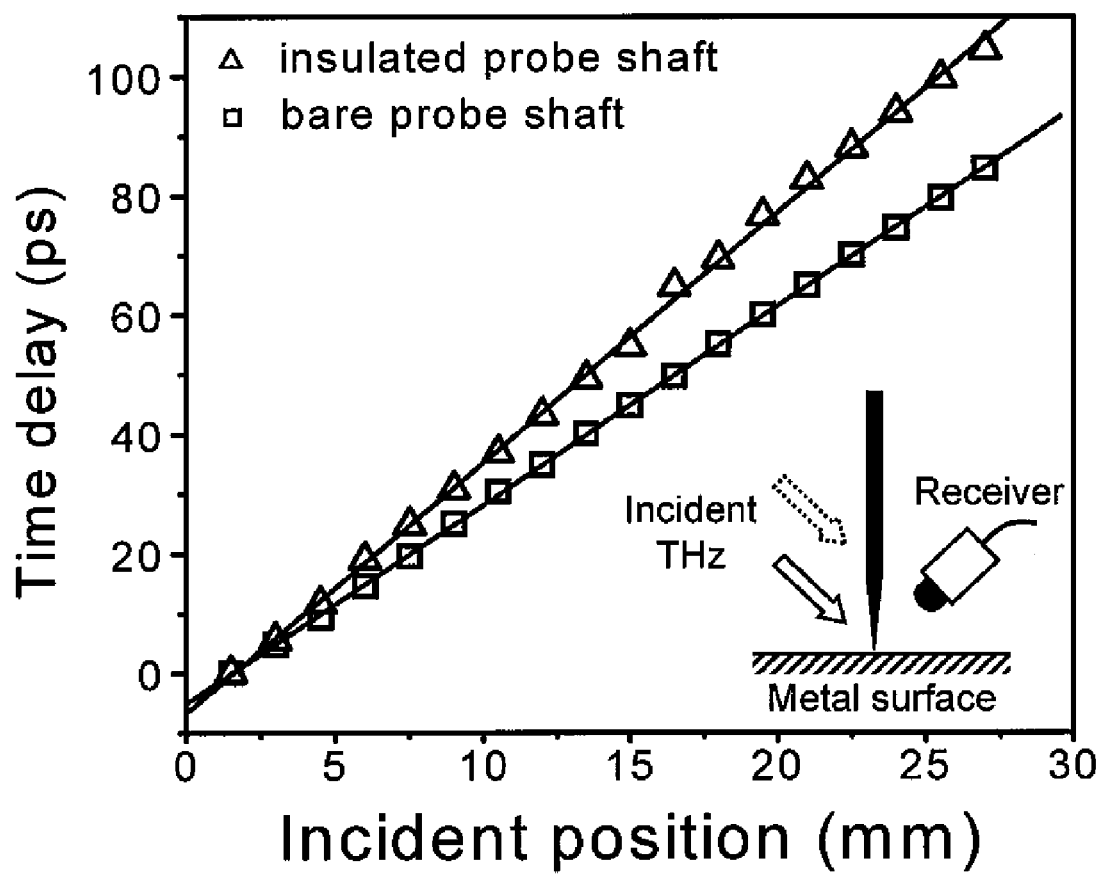
FIG. 12 is a plot of arrival time as a function of incident position for a series of time-domain THz pulses propagating along a bare metal probe (squares) and a probe wrapped with a 0.5 mm PVC insulation layer (triangles), as detected in a THz apertureless near-field scanning optical microscopy system.

A uniaxial waveguide, sometimes referred to herein as a "wire waveguide," may be coupled with a THz antenna in the manner(s) described herein. For example, the center one of a pair of concentric electrodes can be affixed to the end of the waveguide or a radially polarized beam can be focused on the end of the waveguide. The wire waveguide could also be coupled to the THz antenna through the use of a substrate lens, similar to the type of lens typically used in terahertz time-domain spectroscopy. Alternatively, a linearly polarized THz beam may be focused on a scattering object placed near the waveguide. If the beam is sufficiently intense, enough scattered energy will be coupled into the waveguide modes and transported along the waveguide to serve as a detectable signal. This latter technique is illustrated in FIG. 12. Finally, one could couple free-space radiation onto the waveguide through the use of a grating coupling scheme, in which a periodic modulation of some property of the wire (e.g., the diameter) is used to diffract incident radiation along the wire axis, thus exciting the guided mode.

Dual or Parallel Waveguides

Figure 21:
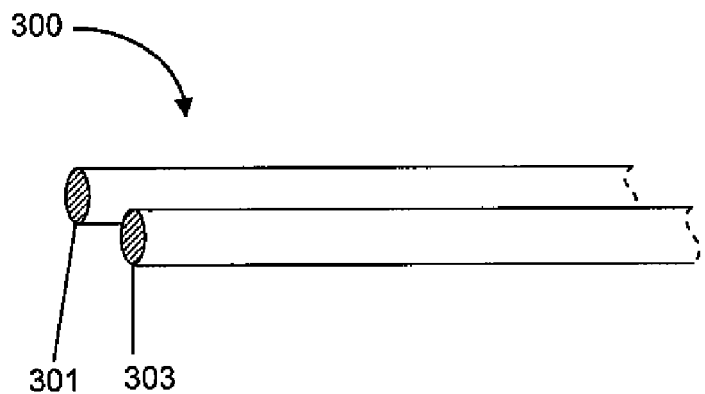
FIG. 21 is a schematic diagram of an embodiment of a dual waveguide.

As shown in FIG. 21, in another embodiment, a waveguide for THz radiation comprises at least a first conductive elongate element 301 and a second conductive elongate element 302 to form a dual waveguide 300. Preferably, the conductive elements 301, 303 are substantially parallel and generally are equidistant from each other (i.e. uniformly spaced from each other along their entire lengths). As used herein, "parallel" means that the conductive elements 301, 303 lie in a common plane and do not intersect. Generally, dual waveguide 300 comprises bare conductive elements. In other words, the conductive elements 301, 303 are not surrounded by an outer wall or covering. Preferably, the elements are long and thin wire-like elements. It is emphasized that the conductive elongate elements are not plates. In an embodiment, each conductive element comprises a solid metal wire or lead. Alternatively, each conductive element 301, 303 comprises a bundle of wires, filaments, leads, or fibers. In some embodiments, conductive elements may be hollow. Moreover, first and second conductive element 301, 303 may have cylindrical, rectangular, hexagonal, triangular, or other cross sectional geometry. Although, dual waveguide 300 has been described thus far as having two conductive elements, it is contemplated that in other embodiments, the waveguide 300 may comprise more than two conductive elements that are all substantially parallel to each other.

Figure 22:
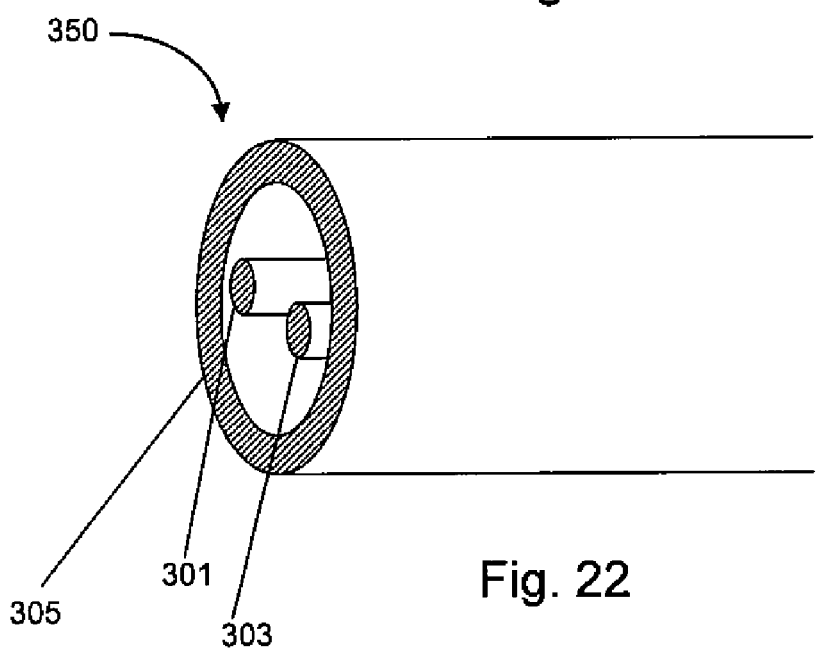
FIG. 22 is a schematic diagram of an embodiment of a coaxial dual waveguide.
Figure 23:
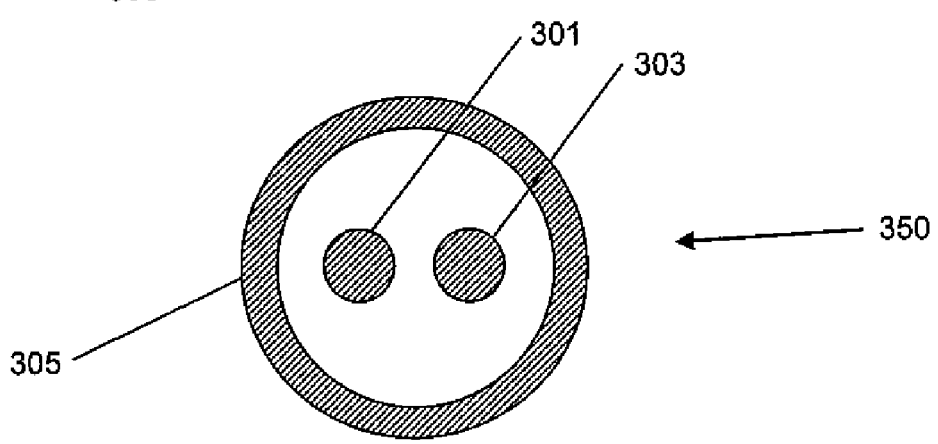
FIG. 23 is a cross-section of an embodiment of a coaxial dual waveguide.

As shown in FIGS. 22-23, the dual elements 301, 303 may be surrounded by an outer wall 305 which is opaque to THz radiation to form a dual coaxial waveguide 350. First and second conductive elements may be fabricated from any high conductivity metal. The conductive elements are preferably spaced such that first and second conductive element are not touching and preferably such that the distance between them is constant. Generally, dual cores 301, 303 are no more than about 1 cm apart, more preferably no more than 0.5 cm apart.

Figure 24:
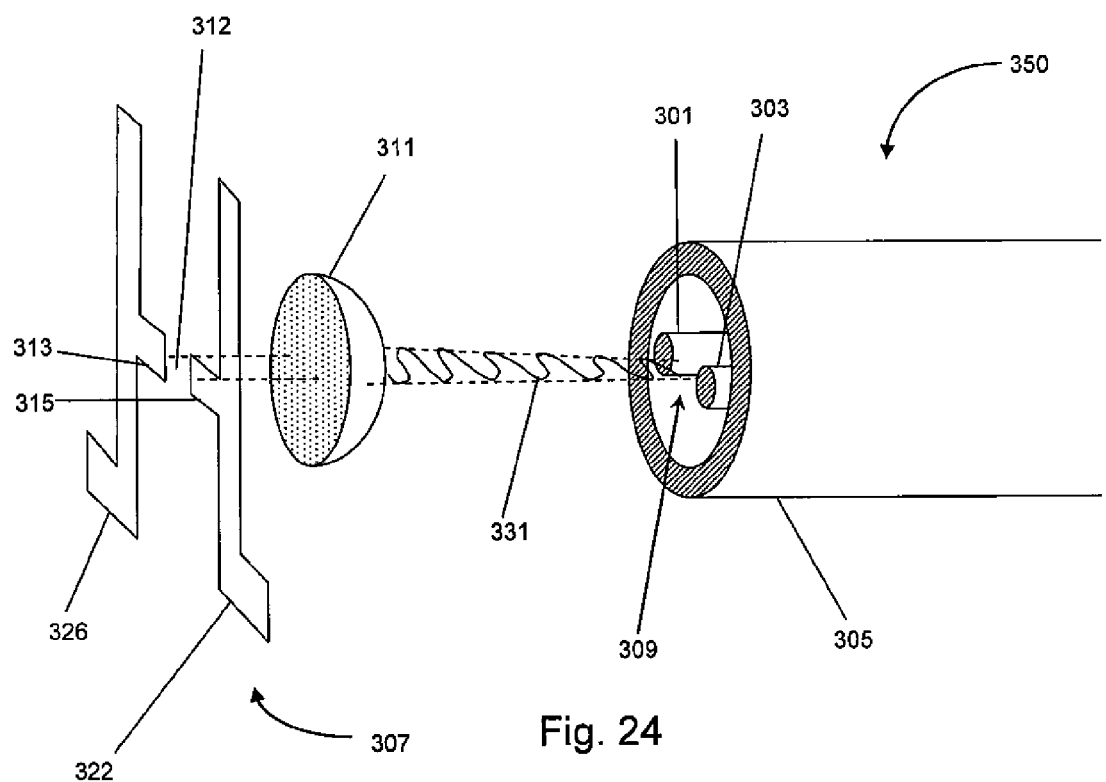
FIG. 24 is a schematic diagram of a linear dipole antenna coupled to a dual waveguide.

One advantage of the dual waveguide is that it does not require a radially polarized source although it can work with one. Therefore, the dual waveguide is capable of being used in conjunction with any type of THz transmitting antennae. In a preferred embodiment, the THz antenna is a conventional dipole THz antenna. Conventional THz dipole antennas emit a linearly polarized beam of THz radiation as opposed to a radially polarized beam generated by a radially symmetric THz antenna as shown in FIG. 1. FIG. 24 illustrates an embodiment a terahertz transmitting system in which a dual waveguide is used with a conventional THz dipole antenna 307. In general, linear dipole antenna 307 is preferably mounted on a semi-conducting substrate such as gallium arsenide or silicon on sapphire. As shown, linear THz dipole antenna 307 comprises first and second electrodes 322, 326. First and second electrodes 322, 326 are substantially parallel to each other. Additionally, first and second electrode 322, 326 each include an electrode extension 313, 315, respectively, which extend substantially perpendicular from first and second electrodes 301, 303. Inner electrodes 313, 315 extend toward each other and are substantially aligned so that gap 312 is defined between them. An ultrashort pump-laser pump is directed at the gap 312. When a voltage is applied across the gap and the laser is fired, a THz pulse is generated.

According to an embodiment, dipole THz antenna 307 is aligned with dual waveguide 350 such that a beam 331 of THz radiation is collimated and focused on the area 309 between the dual conductive elements. In embodiments, dual waveguide 350 may be perpendicular to antenna 307. However, waveguide 350 may be aligned at any suitable angle which is not parallel to antenna 307. The THz beam is collimated using a collimator 50 such as a hemispherical silicon dome as shown in FIG. 24. Collimator 50 may be disposed between dipole THz antenna 307 and dual waveguide 350. The linearly polarized beam 331 propagates down the dual waveguide 350 between the first and second conductive element 301, 303. Without being limited by theory, it is believed that the dual waveguide has reduced loss because of the decreased area of propagation. In her embodiments, dual waveguide 350 may be used with a radially symmetric antenna as disclosed above.

Figure 25:
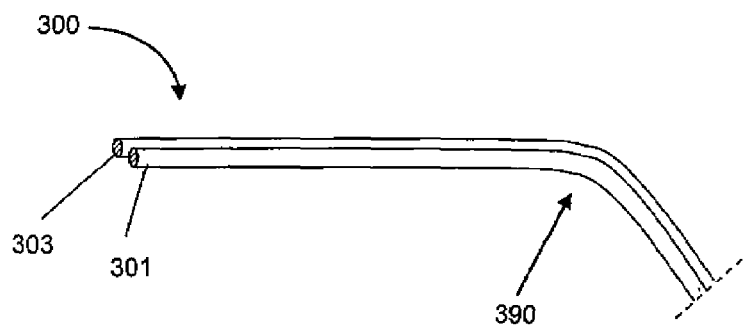
FIG. 25 illustrates an embodiment of a dual waveguide with a bend.

In yet another embodiment, the first and second conductive element 301, 303 of dual waveguide 300 each includes a bend or curve 390 along their respective longitudinal axes while remaining substantially parallel to each other as shown in FIG. 25. As with uniaxial waveguides, another advantage of the dual waveguide 300 may be its ability to transmit linearly or radially polarized THz pulses or signals around corners and angles other than a straight line. Alternatively, first and second conductive element 301, 303 may comprise divergent curves or bends such that first and second conductive element 301, 303 form a split. As will be described below, divergent conductive elements may be useful for interferometry applications.

Figure 26:
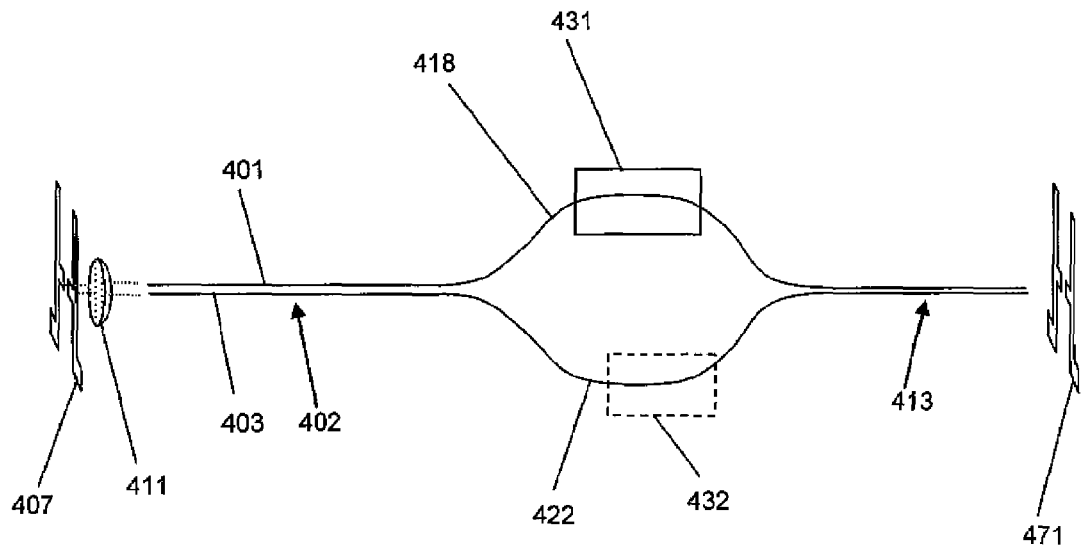
FIG. 26 is a schematic diagram of an embodiment of a Mach-Zehnder interferometer using a dual waveguide.

Referring now to FIG. 26, in one particular application involving a dual waveguide, a Mach-Zehnder interferometer 400 may incorporate a dual waveguide. The dual waveguide may comprise bare first and second conductive elements or coaxial conductive elements. In an embodiment, a THz beam is generated, as described above, with a conventional THz antenna 407 and collimator 411. However, the dual waveguide 402 includes a split between the first conductive element 401 and the second conductive element 403. First conductive element 401 and second conductive element 403 diverge from each other to form a sample waveguide 418 and a reference waveguide 422. Without being limited by theory, it is believed that the linearly polarized THz beam will split into two separate radially polarized beams when first conductive element and second conductive element diverge and the split beam will follow the two paths laid out by the two conductive elements 401, 403.

Still referring to FIG. 25, sample waveguide 418 enters a sample chamber 431 containing a sample compound of interest. The sample compound may be a liquid, a gas or a solid. Reference waveguide 422 remains exposed to ambient air or ensconced in outer wall. Alternatively, reference waveguide 422 may pass through a reference chamber 432 containing a reference material. Sample waveguide 418 exits sample chamber and rejoins reference waveguide 422 to re-form secondary dual waveguide 413. It is envisioned that the two radially polarized beams will merge and become a single linearly polarized beam at this point. Secondary dual waveguide 413 is aligned with a detector 471. Detector 471 typically also comprises a conventional dipole THz antenna. Detector 471 is capable of determining the intensity of the THz beam emitted from the end of dual waveguide 411.

As the THz beam traveling along sample waveguide 418 passes through a material with a refractive index the phase of the THz beam will be shifted. As the THz beam from the sample waveguide 418 rejoins the THz beam from the reference beam, the sample beam will interfere with the reference beam. To the extent that the beams are out of phase, this interference will cause a corresponding decrease in the measured intensity of the THz beam. In an embodiment, the THz interferometer could be used to detect minute differences in concentration between the reference chamber and the sample chamber.

Applications

Embodiments of the disclosed systems have many possible uses. First, the use of guided terahertz pulses eliminates the need for free-space optical components, which vastly simplifies the alignment of a terahertz spectrometer This makes the use of a terahertz system far more realistic for many applications, particularly those for which sensitive alignment is problematic. A good point of comparison in this case is the Fourier Transform Infrared (FTIR) spectrometer, a device found in virtually all undergraduate analytical laboratories, at every university in the US. If a terahertz system were as easy to use as an FTIR, one could imagine that it could also be used as a teaching tool in similar fashion.

In the disclosed THz systems, lateral spreading may be eliminated because the mode is confined, but the finite conductivity of the metal remains as limitation on the efficiency of the waveguide. This constraint could be minimized by using materials with very high conductivity such as copper or silver, or some other lower-conductivity material coated with a thin layer of copper or silver. In the latter case it is preferred that the thin layer be thicker than the skin depth of the high-conductivity material, which is roughly 1 micron. In addition, because the disclosed waveguides can have a small cross-section and because of the simplicity of their design, the disclosed waveguides are more compatible than other recently demonstrated THz waveguides with many envisioned applications, such as endoscopy.

Many terahertz imaging and sensing applications will require transmitting terahertz radiation to and receiving it from a sample that is difficult to reach. Many of these applications require an endoscope-type configuration, to guide the terahertz waves to the sample, and then guide the reflected radiation back to a detector. The disclosed waveguides are perfectly suited for this purpose. For example, a waveguide may be used to transmit THz radiation through openings that are too small for effective transmission of an unguided wave. The wave transmitted in this manner can be received at a remote receiver or by a receiver mounted on the endoscope.

Figure 6:
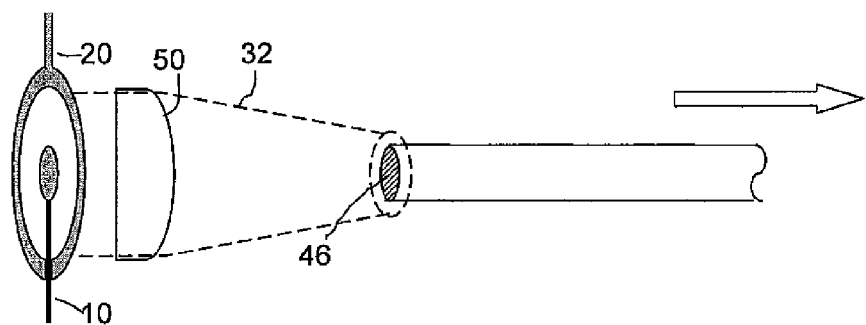
FIG. 6 is a schematic diagram of a coaxial antenna coupled to a uniaxial waveguide.
Figure 7:
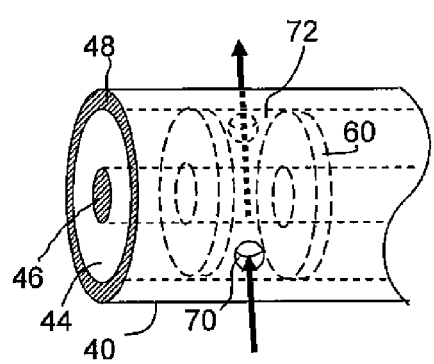
FIG. 7 is a schematic diagram of one embodiment of a coaxial waveguide adapted to serve as a sensor.

In other applications, the waveguide itself can serve as the sampling container. In one such embodiment, illustrated in FIG. 7, the outer wall 48 of the waveguide may be perforated with one or more openings 70 so as to allow the passage of a fluid (liquid or gas) into or through the waveguide, as indicated by the arrows. If desired, two or more plugs 60 can be used to define an inner chamber 72 and limit the axial flow of fluid through the waveguide. In alternative embodiments (not shown), plugs 60 are provided with holes and allow fluid flow along the length of the waveguide, in addition to, or instead of the transverse flow illustrated in FIG. 6.

Probe or Sensor System

Figure 8:
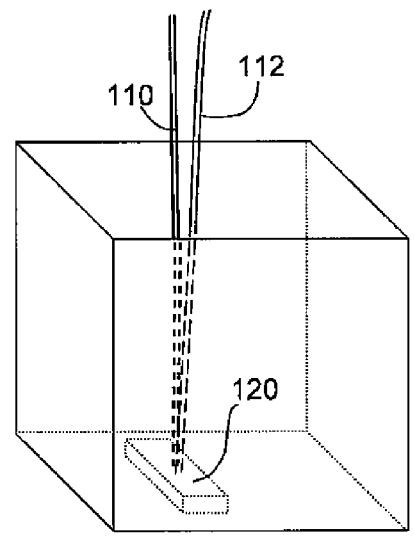
FIG. 8 is a schematic diagram of one embodiment of a THz probe.

FIG. 8 shows a THz probe or sensor system comprising a first waveguide 110 and a second waveguide 112. Waveguides 110, 112 may be coaxial, uniaxial, dual, or dual coaxial waveguides. First waveguide 110 may be used to transmit a THz signal, such as may be provided by a coupled coaxial antenna, to a desired object of interest 120. Second waveguide 112 receives the echo/reflected portion of the signal and transmits it to a receiver (not shown). The received signal contains information about the object of interest 120. A system such as this can be used to facilitate inspection of enclosed spaces or other regions, or of objects that cannot be viewed using line-of-sight techniques or optical inspection systems.

Figure 9:
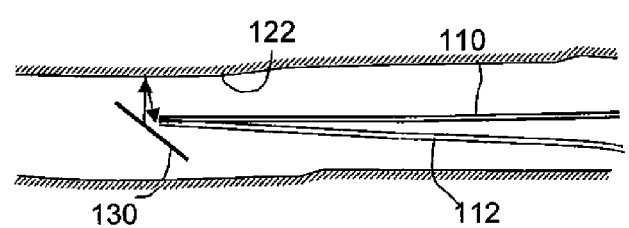
FIG. 9 is a schematic diagram of one embodiment of a THz endoscope.

The system shown schematically in FIG. 8 may, in some embodiments, be combined with a reflector 114, as shown in FIG. 9. Reflector 130 reflects the incident signal from waveguide 110 off an adjacent surface or object 122, from which the signal returns and is reflected into waveguide 112, as indicated by the arrows in FIG. 9. This combination allows inspection of a confined area of interest and is therefore particularly useful for endoscopy. Among other applications, THz endoscopy is proving particularly useful for cancer detection. Recent studies have shown that THz is very useful for skin cancer detection, and it is being investigated for detection of cancers of the colon, esophagus, etc.

THz Apertureless Near-Field Scanning Optical Microscopy

Figure 10:
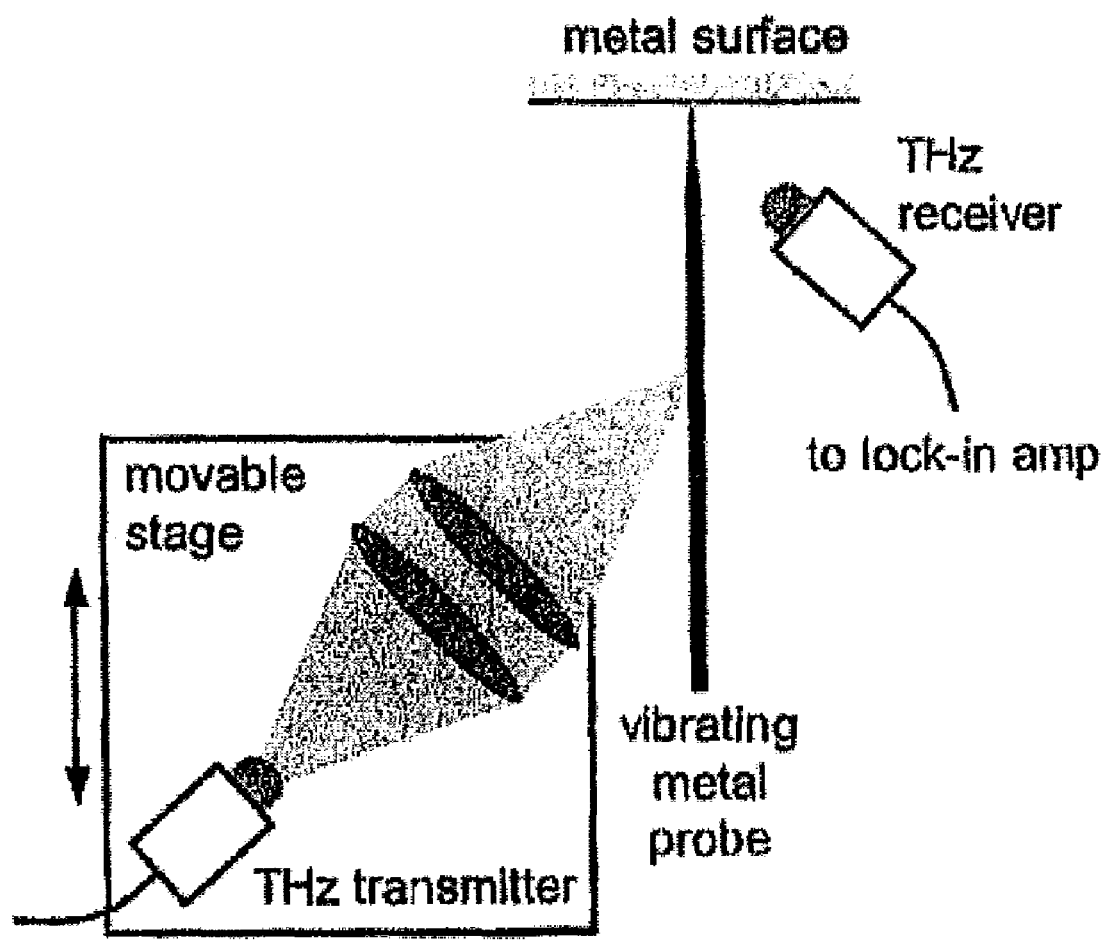
FIG. 10 is a schematic diagram of one embodiment of a THz near-field scanning optical microscope.

According to another embodiment of the invention, a THz waveguide is used as the emitting tip of a near-field scanning optical microscope (NSOM). In this technique, light is scattered off a subwavelength-sized metal tip which is held close to a surface. The scattered light is collected in the far-field, giving subwavelength resolution in the immediate neighborhood of the tip apex. One embodiment of a THz NSOM system is illustrated in FIG. 10; in other embodiments the waveguide could be coupled to a coaxial THz antenna.

Spectral Analysis

Figure 11:
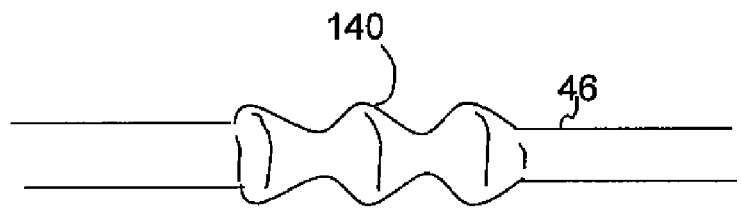
FIG. 11 is a schematic diagram of a second embodiment of a THz waveguide.

A still further embodiment of the invention is achieved when the disclosed waveguides (e.g., uniaxial, dual, dual coaxial) includes a plurality of variations in the diameter of the core or conductive elements 301, 303, as shown in FIG. 11. These form ridges 140, which function as a diffraction grating, causing the THz signal to spread into its spectral components and thus allowing filtering of the signal.

The desired diffraction can be achieved using a variety of techniques. For example, instead of varying the diameter of the metal wire, the exterior surface of the wire with can be coated with another material. The coating may vary in thickness, or may be periodic along the length of the antenna.

EXAMPLE 1

Propagation Effects in Near-Field Optical Antennas

The propagation of THz radiation along bare metal wires was first observed in the demonstration of apertureless near-field scanning optical microscopy (NSOM) using THz-TDS. The experimental setup is depicted in FIG. 12. The broadband single-cycle pulses of free-space THz radiation were generated using a photoconductive transmitter and were focused onto a beryllium-copper probe acting as an apertureless near-field optical antenna. The probe had a tip of about 25 μm radius and a shaft of 0.5 mm diameter coated with a thin layer of tin to prevent oxidation. The sample was a featureless gold-coated silicon wafer, placed in close vicinity of the tip. The mean distance between the tip and the gold surface, d~350 nm, was precisely controlled by a piezoelectric transducer. In such a configuration, the tip strongly interacted with its image in the metal surface, and converted the localized evanescent field around the tip to propagating radiation through a scattering process. The electric field of the scattered THz pulses was detected in the time-domain by a photoconductive receiver which is located near the tip. In the measurement, the probe tip vibrated normally to the surface at 750 Hz to modulate the scattered radiation, and the detected signal is demodulated using a lock-in amplifier. The propagation of THz pulses was observed by moving the incident focal spot up along the shaft of the probe, as shown by the dashed arrow. In this case, some of the incident THz radiation was coupled into a propagating mode on the shaft. This propagating mode moved down the shaft and excited the tip, producing a scattered wave which was detected by the receiver. Different incident positions lead to different propagation times and therefore different time delays in the detected time-domain waveforms. A piece of metal perpendicular to the needle was placed close to the shaft at the incident spot to provide a sharp start point of the propagation. Scattering of the THz radiation at the edge of this metal helped to couple the incident wave into a propagating mode on the shaft. The THz transmitter, the focusing lenses, and this metal scatterer were all mounted on a movable stage so that the incident position along the shaft could be precisely controlled.

The propagation effect was evident from the relative delay of the waveforms obtained by moving the transmitter stage along the shaft of the needle in steps of 1.5 mm. As the point of incidence moved away from the tip, the pulse took longer to propagate along the shaft, and its amplitude decreased. The propagation was largely nondispersive, since the shape of the time-domain waveform did not depend strongly on propagation distance. The group velocity of the propagation mode could be extracted from the time-domain waveforms. The relative time delay of these waveforms showed a linear dependence on the propagation distance, as depicted by the squares in FIG. 12. A least-squares fit to these data yielded the group velocity $v_g=(3.00\pm0.01)\times10^8$ m/s, the free-space velocity of light. A similar measurement was performed in which the needle is wrapped with a 0.5 mm PVC layer. The existence of the insulator layer distorted the detected waveforms, and also reduces the group velocity of the propagation to 0.8c, as depicted by the triangles in FIG. 12. This result indicated that the propagation was confined and guided along the surface of the probe.

Besides the measurements with a bare needle and an insulated needle, propagation measurements were taken with a circular aluminum barrier situated on the probe, the disturbance and the reflection of the propagation mode were then observed. These results revealed the possibility of a new method for THz wave guiding and manipulating. However, the waveforms detected in these experiments were not the electric field of the propagating THz pulses, but the scattered radiation from the probe tip. To eliminate the spectral filtering effects introduced by the probe tip, a new experimental configuration for direct measurement of the THz propagation on bare metal wires was required. This new configuration permitted us to fully characterize the propagating mode along the wire waveguide.

EXAMPLE 2

Direct Characterization of a THz Wire Waveguide

For a better observation and characterization of the guided THz propagation on metal wires, we changed the experimental setup from the NSOM configuration to a new configuration in which the electric field of the guided mode was directly detected at the end of the waveguide. With the fiber-coupled transmitter and receiver, the incident position (the start point of the propagation) and the detection position of the THz pulses were changed to observe the spatial profile of the guided mode. A long stainless steel wire with a smooth surface, rather than the tiny tapered probe in the NSOM experiments, was used as the waveguide for the new measurements.

Experimental Setup

Figure 13:
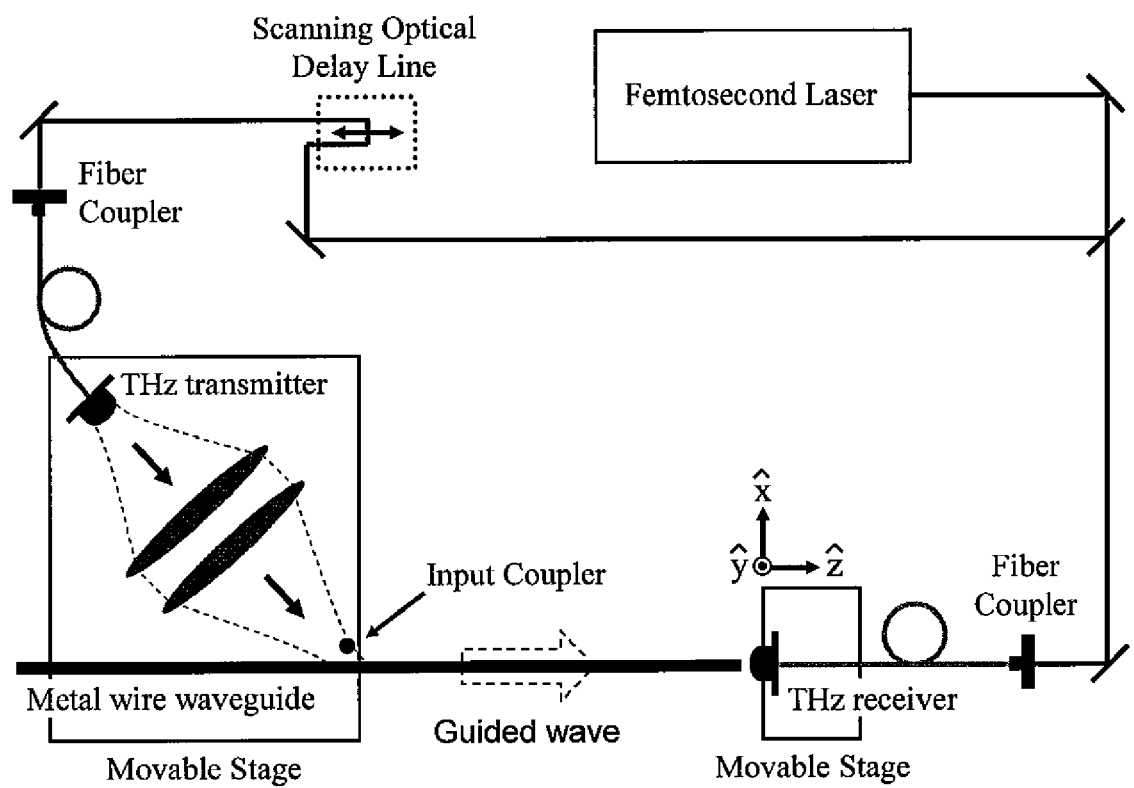
FIG. 13 is a schematic diagram of an experimental setup for characterization of a THz wire waveguide.

A schematic illustration of the new experimental setup is shown in FIG. 13. As in the NSOM experiments, the broadband single-cycle pulses of free-space THz radiation were generated and coherently detected using ultrafast photoconductive sampling. The horizontally polarized THz pulses were focused onto the stainless steel waveguide. Another stainless steel wire was placed at the focal spot, oriented perpendicular to the waveguide (the y direction in FIG. 13). This second wire served as an input coupler. As such, it could be replaced with a fill or partial foil or mesh screen, or any other device capable of coupling the mode of the radiation to the mode of the waveguide. Scattering of the input THz radiation at the intersection structure helped to excite the radially polarized mode which can propagate along the waveguide. Both the waveguide and the coupler are 0.9 mm in diameter, and the separation between them is 0.5 mm. The receiver was placed at the end of the waveguide and was oriented to detect only the vertically polarized component of the electric field in order to eliminate the possibility of detecting directly scattered radiation which would interfere with the detection of the guided mode. The incident THz beam was modulated by a chopper in front of the transmitter and a lock-in amplifier was used for detecting the induced photocurrent in the receiver. The THz transmitter, the focusing lenses, and the coupler were all mounted on a movable stage so that the incident position along the waveguide could be controlled. The THz receiver was mounted on a three-axis stage for detection at various positions with respect to the end of the waveguide.

Spatial Profile

Figure 14:
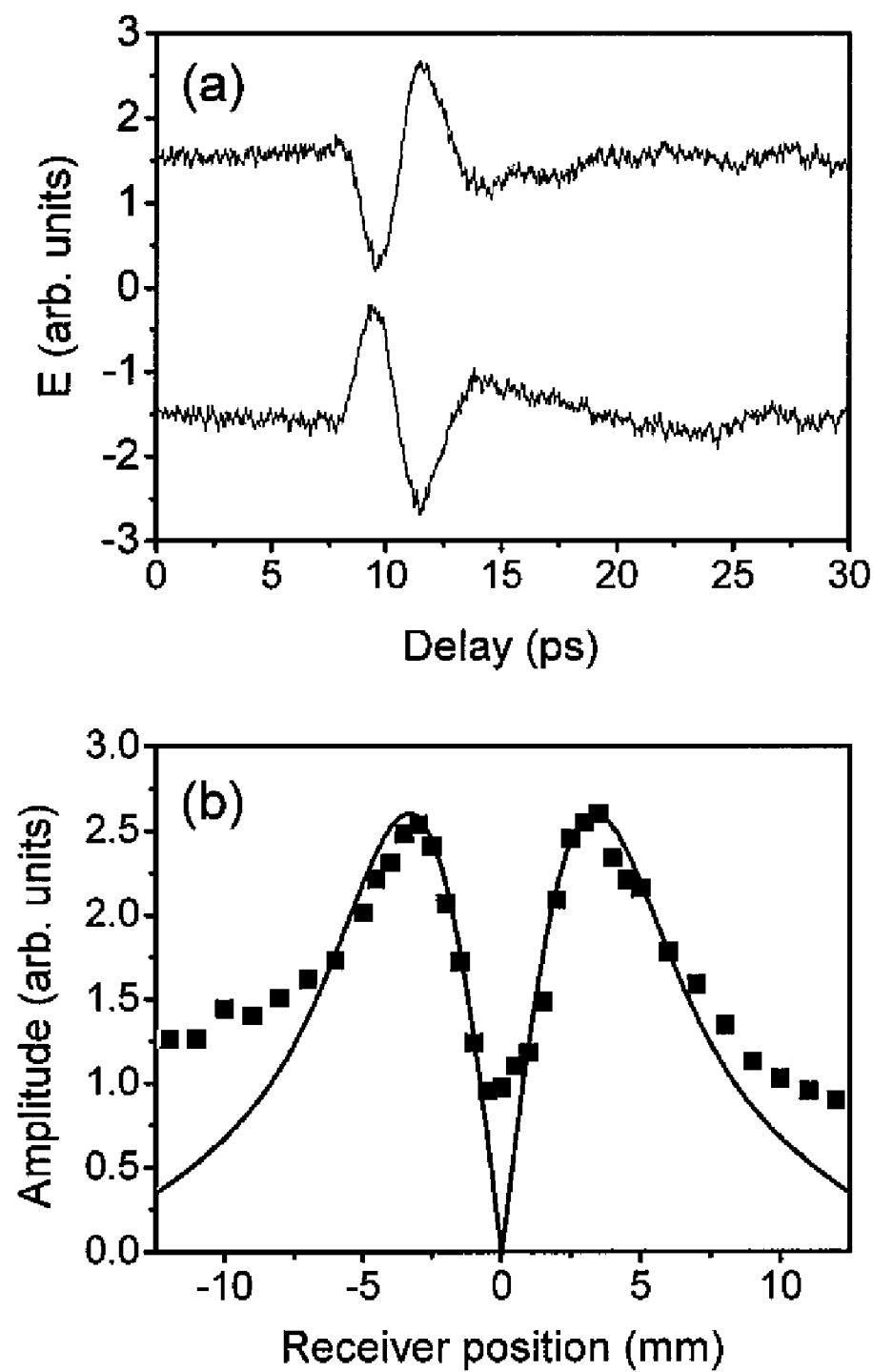
FIG. 14 is two plots showing the spatial profile of the propagating mode on a metal wire waveguide.

As the first step in characterizing the propagating mode on the wire waveguide, we measured the spatial profile of the electric field around the waveguide by vertically scanning the THz receiver at the end of the waveguide. FIG. 14(a) shows typical time-domain electric field waveforms, for two different receiver positions located 3 mm above and 3 mm below the wire waveguide. These waves are vertically (y) polarized, perpendicular to the horizontally (x) polarized input beam. The polarity reversal as the detector scans across the wire clearly shows the radial nature of the guided mode. The peak-to-peak amplitude of the waveform as a function of the vertical displacement of the receiver is depicted by the squares in FIG. 14(b). The amplitude decreases with the transverse displacement approximately as 1/r. Since the polarization response of the photoconductive receiver antenna is not perfectly symmetric, the measured electric field is not precisely zero at the center point in the experiment. This can also explain the slight asymmetry in the amplitude profile of the detected waveforms.

The observed behavior can be understood in terms of either the TEM mode of a coaxial waveguide or in terms of a Sommerfeld wave. The TEM mode in a coaxial waveguide is radially polarized, and the electric field varies as the inverse of the radial position, as $$E_r = \frac{V}{r \ln \frac{a}{b}} \quad (1)$$

where a and b are the radii of the outer and inner conductors, respectively, and V is a position-independent voltage. Although providing a qualitative picture, this description cannot be extended to cover the case of interest here because this expression vanishes in the relevant limit, a→∞. A more accurate picture can be obtained from Sommerfeld's description of an electromagnetic wave propagating along the surface of a cylindrical conductor, a so-called Sommerfeld wire wave. In this case, it has been shown that the important propagating solution is an axially symmetric TM wave. Outside the metal, the variation of the radial electric field component (the dominant component) is described by a Hankel function, $H_1^{(1)}(\gamma r)$, where γ is defined in terms of the propagation constant k of the field outside the wire according to $\gamma^2 = \omega^2/c^2 - k^2$. For a perfectly conducting wire, γ=0 and the field propagates with a velocity determined solely by the external medium (in our case, air). For large but finite conductivity, γ is small and the approximate form for the Hankel function can be used, appropriate for small argument:

$$H_1^{(1)}(x) \approx -2i/\pi x \quad (2)$$

Thus, a Sommerfeld wire wave also exhibits 1/r decay, within a distance $r_0 << |1/\gamma|$ of the wire surface.

The Sommerfeld description can be used to estimate the distance that the wave extends from the metal surface, for a metal of finite conductivity. To do so, one must determine γ by solving the transcendental equation which results from the boundary conditions at the wire surface. Following the method described by Goubau, the amplitude of the wave was computed as a function of radial distance, for the case of a 0.9 mm-diameter stainless steel (type 304) cylinder, with a conductivity of $1.39 \times 10^6$ mho/m, about 2.4% of the conductivity of copper. To account for the finite aperture of our detector, we convolve this Hankel function with a Gaussian of 6 mm full-width at half-maximum. The resulting profile is shown as a solid curve in FIG. 13(b). We can also calculate the radius inside of which 50% of the power is guided. At a frequency of 0.3 THz, half of the power is transmitted through an area extending roughly 1.2 millimeters from the axis of the wire. The reasonably good agreement between the experimental results and the calculations suggests that the surface wave picture is an appropriate model for our experimental situation. However, as discussed below, the frequency-dependent attenuation is still lacking a quantitative description.

Propagation Characteristics

Figure 15:
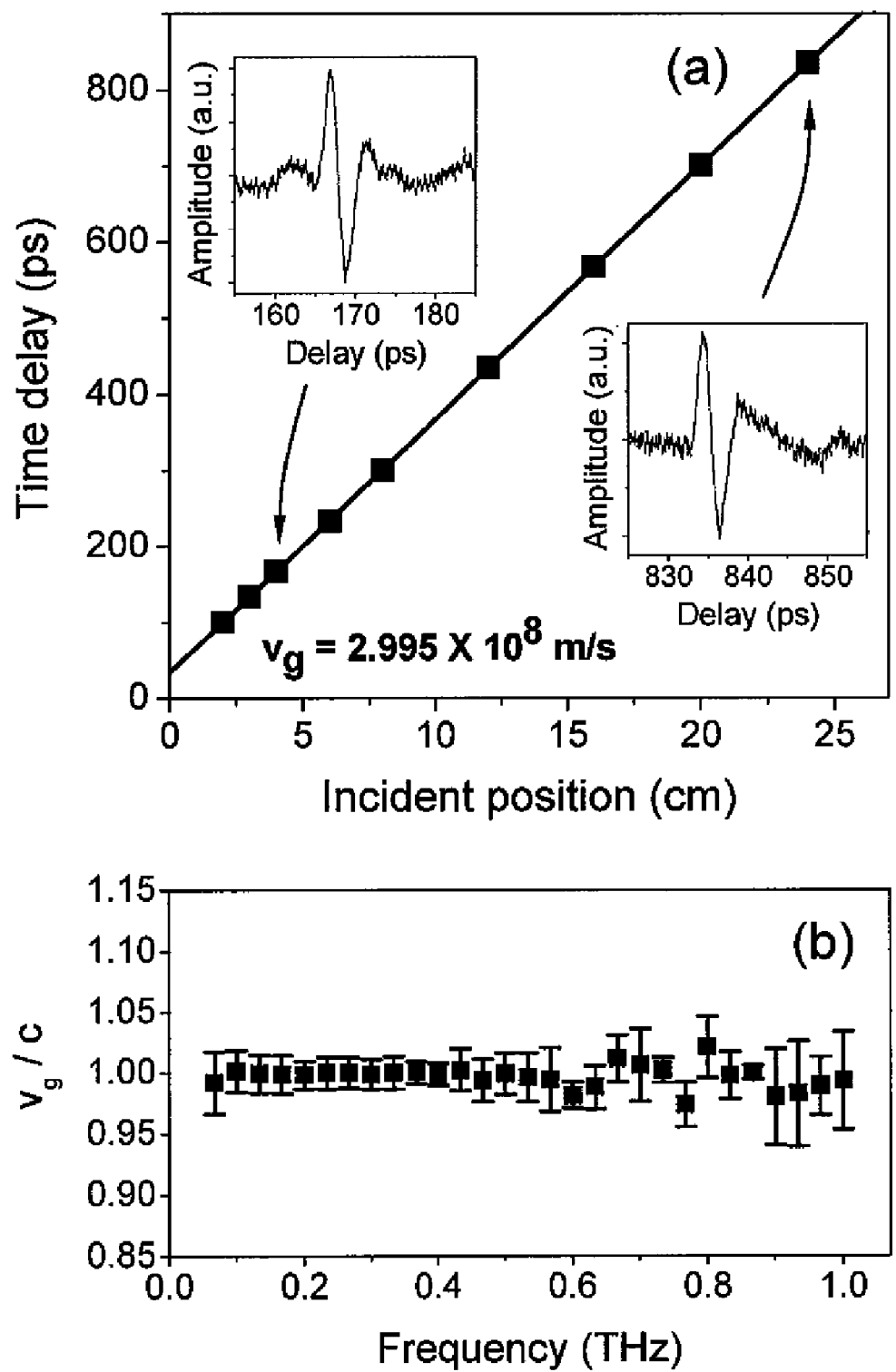
FIG. 15 is two plots illustrating the group velocity of propagating THz pulses on a metal wire waveguide.

The propagation characteristics of the guided mode were studied by moving the incident position of the THz beam along the waveguide. In this way, the time-domain waveforms as a function of propagation distance were obtained. There was no evident change in the temporal shape of the waveforms for propagation up to 24 cm, the limit of our optical delay line. This showed that the propagation was largely dispersionless. As in the NSOM experiment, the broadband group velocity of the propagation mode was determined by analyzing the dependence of the relative time delay of the waveforms on the propagation distance. A least-squares linear fit to these data yields the group velocity $v_g = (2.995 \pm 0.001) \times 10^8$ m/s, as shown in FIG. 15(a). FIG. 15(a) showed the arrival time as a function of incident position for a series of time-domain THz pulses detected using the setup illustrated in FIG. 13 (squares). The spectrum-weighted average group velocity of the guided mode was obtained from the least-squares linear fit to these data. The THz waveforms detected after 4 cm and 24 cm of propagation are shown in the insets. To study the group velocity dispersion, the group velocity for different frequency components was extracted by analyzing the spectra of these waveforms, using $$v_g = \frac{c}{n_{eff}(\omega) + \omega \frac{dn_{eff}}{d\omega}} \quad (3)$$

where $n_{eff}$ is defined as $$n_{eff}(\omega) = \Delta\phi(\omega) \frac{c}{\omega d} \quad (4)$$

Δφ(ω) is the phase change for propagation distance d at angular frequency ω. FIG. 15(b) shows the extracted data, confining that there is no measurable group velocity dispersion throughout the accessible spectral range. This was to be expected, given that the Sommerfeld surface wave model predicts a group velocity deviating from c by less than one part in $10^4$, for our experimental situation.

In order to study the evolution of the guided mode in propagation, we compared the spatial profile of the guided mode detected at different propagation distances, each obtained in the same manner as that in FIG. 14(b). These profiles are depicted by the curves in FIG. 16. It is immediately clear that the electric field is more closely confined to the surface of the wire for the shortest propagation distances. Subsequently, the guided mode spreads laterally, especially during the first several centimeters of propagation, and approaches a spatial profile described roughly by 1/r.

For each propagation distance, the waveform with the maximum peak-to-peak amplitude was extracted. Except for the few shortest propagation distances, these were obtained at a fixed receiver offset of roughly 3 mm (see FIG. 16). These amplitudes were plotted as a function of propagation distance in FIG. 17(a). The amplitude attenuation coefficient $\alpha$ of the wire waveguide can be extracted from these data, simply by fitting the dependence of the pulse amplitude E on the propagation distance x to:

$$E(x) = E_0 e^{-\alpha x} \quad (5)$$

Figure 17:
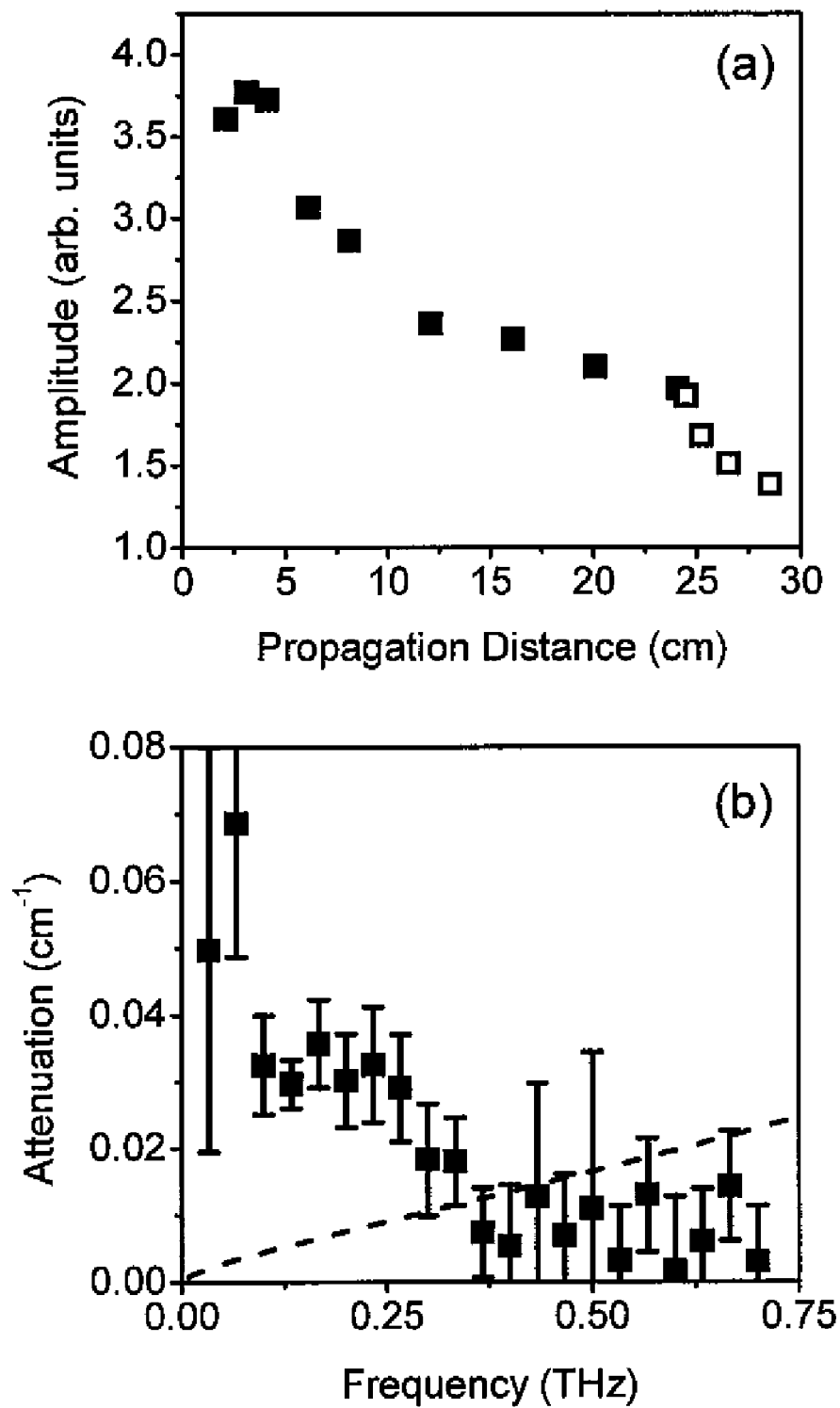
FIG. 17 is two plots illustrating the attenuation characteristic of the guided wave on a metal wire waveguide.

The value we obtained, $\alpha = 0.03$ cm$^{-1}$, was the lowest of any waveguide for broadband THz pulses reported to date. This method gave us the spectrum-weighted amplitude attenuation coefficient, but a more detailed characterization was required to obtain the frequency dependence of the loss. We extracted the attenuation coefficient of each frequency component from the amplitude spectra of the THz waveforms detected at various propagation distances. The spectrum of the attenuation coefficient is shown in FIG. 17(b). We note that the attenuation decreased with increasing frequency.

Figure 16:
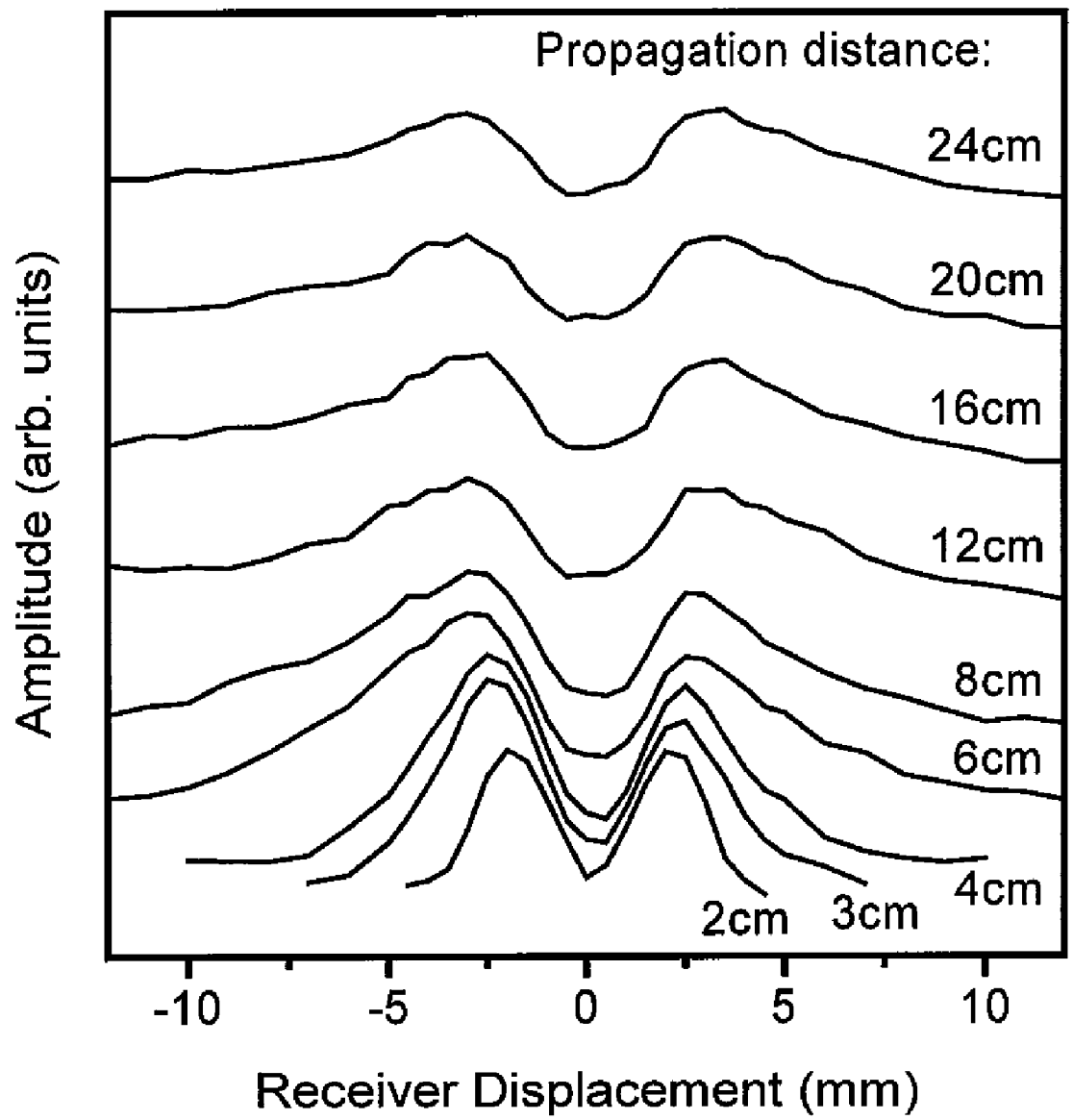
FIG. 16 is a plot of the amplitude of a THz pulses as a function of the vertical displacement of the receiver, measured at different propagation distances.

The low attenuation obtained here emphasized one unique aspect of the wire waveguide. Compared to other waveguide geometries, a metal wire had a much smaller surface area interacting with the electromagnetic field, so the propagation loss due to finite conductivity of the metal was negligible. This is consistent with Sommerfeld's wire wave model, which predicted a very small propagation loss due to the finite conductivity of the metal wire. However, the spectrum of the attenuation obtained in our experiment can not be described simply by the Sommerfeld model, as shown in FIG. 17(b). The predicted losses increased with increasing frequency, similar to other THz waveguides where the attenuation is dominated by ohmic effects. In contrast, the observed losses decrease with increasing frequency. This indicated that much of the measured losses arise from other sources, such as diffractive spreading of the propagating mode in the lateral dimensions, as seen in FIG. 16. The significance of this loss mechanism for Sommerfeld waves has been discussed previously. By moving the receiver away from the end of the waveguide, we observe a sharper drop in the amplitude of the detected pulses, as depicted by the hollow squares in FIG. 17(a), indicating an increasing divergence when the mode propagates off the end of the waveguide.

The measurements do not reflect the losses associated with the coupling of the linearly polarized free-space THz beam to the guided mode. In the experiment described here, only about one percent of the power is coupled to the radially polarized waveguide mode from the free-space incident beam. The more effective mode-matching needed to improve the input coupling can be obtained using the mode-matched antennas described above.

EXAMPLE 3

Manipulation of the Guided Pulses

The manipulation of the guided mode was next studied. The ability to direct radiation along curves is one of the most important features for a practical waveguide. The amplitude of THz pulses was compared after propagating on a waveguide bent with different radii. The results are shown by the hollow triangles in FIG. 18. The propagation distance was 21 cm, and the radius of curvature R was varied from 90 cm down to 20 cm in steps of 10 cm. The amplitude of the electric field E' as a function of the propagation distance x along the bent waveguide is described by $$E'(x) = E_0 e^{-\alpha' x} \quad (6)$$

where $\alpha'$ is the amplitude attenuation coefficient for a bent waveguide. By comparing equation (6) to equation (5) we find $$\alpha' = \alpha + \frac{\ln\left(\frac{E}{E'}\right)}{x} \quad (7)$$

So the amplitude attenuation coefficient for each bend radius was extracted by comparing the amplitude of the detected THz pulse to that of a straight waveguide with the same propagation distance x. The extracted data are depicted by solid squares in FIG. 18. Even a slight bend on the waveguide lead to a considerable increase in the loss, from 0.03 cm$^{-1}$ for a straight waveguide to nearly 0.05 cm$^{-1}$ for a bend radius of 90 cm.

The bend loss can be explained by the continuous conversion of the guided propagation into radiation modes as the wave travels around a curve. This is easy to understand by considering the wavefront of the transverse field, which must rotate around the center of the curvature during propagation. Consequently, at some distance from the center of curvature the phase velocity would exceed c, the propagation speed of the guided mode. So the portion of the field outside this point must be radiated, causing the power loss in the guided mode. This loss mechanism resembles that of a bent dielectric optical waveguide, in which the attenuation coefficient $\alpha$ can be described by a semi-empirical form:

$$\alpha = c_1 \exp(-c_2 R) \quad (8)$$

where R is the radius of curvature and $c_1$ and $c_2$ are constants independent of R. A fit using equation (8) shows a good agreement with the experimental data, as seen in FIG. 18, suggesting that radiation is the dominant mechanism for the propagation loss of a bent metal wire waveguide.

From the spatial profile of the propagation (FIG. 14(b) and FIG. 16) we can see that the guided mode has a large extent compared to the cross section of the waveguide. Hence we predict that the guided mode would be easily coupled between two curved waveguides in contact with each other (or between a curved waveguide and a straight one). These features enable the Y-splitter for the wire waveguide, as illustrated in FIG. 19. The validity of this scheme has been verified by electric field measurements with such a structure. The waveforms in FIG. 20 are detected at points A, B, and C in FIG. 19, namely: at the end of the straight waveguide (A), at the end of the curved waveguide (B), and at a position between them (C). The separation between A and B is 2 cm, and the waveforms are detected with the THz receiver 3 mm below the plane of the splitter structure. The plot clearly shows that part of the propagating power on the straight waveguide is coupled to the branch waveguide by the Y-splitter.

Besides the waveguide described above, we have also tried many other metal wires as THz waveguides. The materials for these guides include steel, aluminum, copper, zinc and nickel-chrome alloys. The wire diameter of these guides ranges from 0.5 mm to 6.4 mm. In situations where the guided mode could be perturbed by other structures close to the waveguide, an outer metallic shield could be provided, forming a coaxial waveguide, as long as the additional ohmic losses could be tolerated.

With a Y-splitter structure used to separate the output wave from the input wave, and a small mirror attached at the end of the waveguide as a 90-degree output director, we have successfully demonstrated a THz endoscope, by detecting THz pulses reflected from the bottom and the side wall inside a container. Further improvement could be made by combining an endoscope with an imaging system. This may be accomplished by scanning the endoscope along the surface of the detected region, or alternatively, scanning or rotating the sample to obtain an internal THz image. One challenge for this application is the low power transmitted by the endoscope which strongly limits the data acquisition rate as well as the dynamic range. With optimization of the mode of the input beam and the coupling geometry using the invention described above, the power launched into the endoscope probe can be greatly increased.

It is also interesting to note that this waveguide naturally generates a radially polarized mode. So with a focusing lens mounted at the distal end of an endoscope, a higher resolution can be obtained than in the normal THz imaging system, due to the sub-diffraction-limited focusing of radially polarized beams. Furthermore, since the radially polarized mode is an ideal input field for a coaxial near-field probe or an apertureless near-field optical antenna, nanometer-resolved endoscopic THz imaging may be possible. This would pave the way for a wide range of new applications for terahertz sensing and imaging.

While embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference in the Description of the Related Art is not an admission that it is prior art to the invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

REFERENCES

The following references provide background information and are each incorporated herein by reference in their entireties, except to the extent that they define terms differently than those terms are defined herein:

1. Miyaji, G; Miyanaga, N; Tsubakimoto, K; et al. *Intense Longitudinal Electric Fields Generated From Transverse Electromagnetic Waves* APPL PHYS LETT, 84 (19): 3855-3857 May 10, 2004
2. Dorn, R; Quabis, S Leuchs, G *Sharper Focus For A Radially Polarized Light Beam* PHYS REV LETT, 91 (23): art. no.-233901 Dec. 5, 2003
3. Armstrong, D J; Phillips, M C; Smith, A V *Generation Of Radially Polarized Beams With An Image-Rotating Resonator* APPL OPTICS, 42 (18): 3550-3554 Jun. 20, 2003
4. Moshe, I; Jackel, S; Meir, A *Production Of Radially Or Azimuthally Polarized Beams In Solid-State Lasers And The Elimination Of Thermally Induced Birefringence Effects* OPT LETT, 28 (10): 807-809 May 15, 2003
5. Grosjean, T; Courjon, D; Spajer, M *An All-Fiber Device For Generating Radially And Other Polarized Light Beams* OPT COMMUN, 203 (1-2): 1-5 Mar. 1, 2002
6. Bomzon, Z; Keiner, V; Hasman, E *Formation Of Radially And Azimuthally Polarized Light Using Space-Variant Subwavelength Metal Stripe Gratings* APPL PHYS LETT, 79 (11): 1587-1589 Sep. 10, 2001
7. Oron, R; Blit, S; Davidson, N; et al. *The Formation Of Laser Beams With Pure Azimuthal Or Radial Polarization* APPL PHYS LETT, 77 (21): 3322-3324 Nov. 20, 2000

What is claimed is:

1. A terahertz (THz) transmitting system comprising:
   an antenna capable of generating a beam of THz radiation; and
   a waveguide aligned with said beam, said waveguide having at least a first and a second conductive elongate element, wherein said first and second conductive elongate elements are substantially parallel, and wherein the first and second conductive elongate elements are configured to propagate a radially polarized beam of THz radiation and a linearly polarized beam of THz radiation.

2. The terahertz transmitting system of claim 1, wherein said at least first and second conductive elements comprise a conductive metal.

3. The terahertz transmitting system of claim 1, wherein said antenna generates a beam of linearly polarized THz radiation.

4. The terahertz transmitting system of claim 1, wherein said antenna comprises a linear dipole photoconductive THz antenna.

5. The terahertz transmitting system of claim 1, wherein said antenna generates a beam of radially polarized THz radiation.

6. The terahertz transmitting system of claim 1, wherein said waveguide comprises an outer wall, wherein said outer wall is impermeable to THz radiation.

7. The terahertz transmitting system of claim 1, wherein said first and second conductive elements form a bend.

8. The terahertz transmitting system of claim 1, wherein said first and second conductive elements are substantially uniformly spaced along their lengths.

9. The terahertz transmitting system of claim 1, further comprising a collimator disposed in between said antenna and said waveguide to focus said beam of THz radiation.

10. The terahertz transmitting system of claim 1, wherein said first and second conductive elements are wires.

11. The terahertz transmitting system of claim 1, wherein said a first and second conductive elements each have a circular cross section.

12. The terahertz transmitting system of claim 1, wherein said first and second conductive elements diverge.

13. The terahertz transmitting system of claim 1, wherein said waveguide comprises more than two conductive elements.

14. The terahertz transmitting system of claim 1, wherein at least a portion of the waveguide has a central region and a peripheral region, and wherein the first conductive elongate element and the second conductive elongate element are located in the central region.

15. The terahertz transmitting system of claim 1, wherein at least a portion of the waveguide has a center axis, and wherein neither the first conductive elongate element nor the second conductive elongate element occupy the center axis.

16. A method for transmitting a terahertz signal comprising:
   a) aligning an antenna capable of generating a beam of THz radiation with a waveguide comprising at least a first and second conductive element;
   b) generating a beam of THz radiation by focusing a laser at said antenna;
   c) collimating and focusing said beam between the first and second conductive elements of said waveguide, wherein the first and second conductive elements are configured to propagate a radially polarized beam of THz radiation and a linearly polarized beam of THz radiation; and
   d) transmitting said beam along the length of said waveguide by propagating said beam between the first and second conductive elements.

17. The method of claim 16, wherein said antenna comprises a linear dipole photoconductive THz antenna.

18. The method of claim 16, wherein (b) comprises generating a beam of linearly polarized THz radiation.

19. The method of claim 18, wherein said laser is an ultrashort pulsed laser beam.

20. The method of claim 18, further comprising splitting the linearly polarized beam into a first and a second radially polarized beam, wherein the first radially polarized beam propagates down the first waveguide and the second radially polarized beam propagates down the second waveguide.

21. The method of claim 16, wherein the first and second conductive elements diverge to form a first waveguide and second waveguide.

22. The method of claim 16, wherein (b) comprises generating a beam of radially polarized THz radiation.

23. A terahertz interferometer comprising:
   a THz emitter that generates THz radiation;
   a primary waveguide aligned with said emitter, said waveguide comprises at least a first and second conductive element, wherein the first and second conductive elements are configured to propagate a radially polarized beam of THz radiation and a linearly polarized beam of THz radiation, and wherein said at least first and second conductive elements diverge to form a sample waveguide and a reference waveguide;
   a sample chamber, wherein said sample waveguide passes through said sample chamber, wherein said sample waveguide and said reference waveguide rejoin to form a secondary waveguide; and
   a detector capable of receiving THz radiation, said detector aligned with said secondary waveguide.

24. The terahertz interferometer of claim 23, wherein said THz emitter comprises a linear dipole THz antenna.

25. The terahertz interferometer of claim 23, wherein said detector comprises a linear dipole THz antenna.

26. The terahertz interferometer of claim 23, wherein said reference waveguide passes through a reference chamber.

27. The terahertz interferometer of claim 26, wherein said reference chamber contains a solid, a liquid, or a gas.

28. The terahertz interferometer of claim 23, wherein said sample chamber contains a solid, a liquid, or a gas.

* * * * *

UNITED STATES PATENT AND TRADEMARK OFFICE
CERTIFICATE OF CORRECTION

PATENT NO. : 7,531,803 B2
APPLICATION NO. : 11/777684
DATED : May 12, 2009
INVENTOR(S) : Daniel M. Mittleman et al.

It is certified that error appears in the above-identified patent and that said Letters Patent is hereby corrected as shown below:

Please insert the following into Column 1 at line 11:

--STATEMENT REGARDING FEDERALLY SPONSORED RESEARCH OR DEVELOPMENT

This invention was made with government support under Grant Number NMA501-03-1-2012 awarded by the U.S. Department of the Interior. The government has certain rights in the invention.--

Signed and Sealed this

Eighth Day of December, 2009

David J. Kappos
*Director of the United States Patent and Trademark Office*